United States Patent
Nagase et al.

(10) Patent No.: US 10,408,742 B2
(45) Date of Patent: Sep. 10, 2019

(54) OPTICAL GAS CONCENTRATION MEASURING METHOD BY FORMING A DIFFERENTIAL SIGNAL USING LIGHTS WITH DIFFERENT ABSORBABILITIES TO A RAW MATERIAL IN A GAS FLOW PATH USING A TIME-SHARING METHOD

(71) Applicants: FUJIKIN INCORPORATED, Osaka, Osaka (JP); TOHOKU UNIVERSITY, Sendai, Miyagi (JP)

(72) Inventors: Masaaki Nagase, Osaka (JP); Kouji Nishino, Osaka (JP); Nobukazu Ikeda, Osaka (JP); Michio Yamaji, Osaka (JP); Shigetoshi Sugawa, Sendai (JP); Rihito Kuroda, Sendai (JP)

(73) Assignees: FUJIKIN INCORPORATED, Osaka (JP); TOHOKU UNIVERSITY, Sendai (JP)

( * ) Notice: Subject to any disclaimer, the term of this patent is extended or adjusted under 35 U.S.C. 154(b) by 112 days.

(21) Appl. No.: 15/524,815

(22) PCT Filed: Nov. 20, 2015

(86) PCT No.: PCT/JP2015/082742
§ 371 (c)(1),
(2) Date: May 5, 2017

(87) PCT Pub. No.: WO2016/080532
PCT Pub. Date: May 26, 2016

(65) Prior Publication Data
US 2017/0315051 A1    Nov. 2, 2017

(30) Foreign Application Priority Data
Nov. 23, 2014    (JP) ................. 2014-237220

(51) Int. Cl.
*G01N 21/3504* (2014.01)
*G01N 21/27* (2006.01)
(Continued)

(52) U.S. Cl.
CPC ............. *G01N 21/27* (2013.01); *C23C 16/18* (2013.01); *C23C 16/52* (2013.01); *G01N 21/314* (2013.01);
(Continued)

(58) Field of Classification Search
CPC ... G01N 21/27; G01N 21/314; G01N 21/3151
(Continued)

(56) References Cited

U.S. PATENT DOCUMENTS 3,895,233 A    7/1975    Boll et al.
4,297,579 A    10/1981    Spaeth
(Continued)

FOREIGN PATENT DOCUMENTS

EP    0 020 877    1/1981
JP    49-106382    10/1974
(Continued)

*Primary Examiner* — Que Tan Le
(74) *Attorney, Agent, or Firm* — Venable LLP

(57) ABSTRACT

To provide a concentration measurement method with which the concentrations of predetermined chemical components can be measured non-destructively, accurately, and rapidly by a simple means, up to the concentrations in trace amount ranges, as well as a concentration measurement method with which the concentrations of chemical components in a measurement target can be accurately and rapidly measured in real time up to the concentrations in nano-order trace amount ranges, and which is endowed with a versatility that can be realized in a variety of embodiments and modes. In the present invention, a measurement target is irradiated, in a time sharing manner, with light of a first wavelength and light of a second wavelength that have different optical
(Continued)

absorption rates with respect to the measurement target. The light of each wavelength, arriving optically via the measurement target as a result of irradiation with the light of each wavelength, is received at a shared light-receiving sensor. A differential signal is formed, the differential signal being of a signal pertaining to the light of the first wavelength and a signal pertaining to the light of the second wavelength, the signals outputted from the light-receiving sensor upon receipt of the light. The concentration of a chemical component in the measurement target is derived on the basis of the differential signal.

6 Claims, 18 Drawing Sheets

(51) Int. Cl.
  *C23C 16/52* (2006.01)
  *G01N 21/33* (2006.01)
  *H01L 21/205* (2006.01)
  *C23C 16/18* (2006.01)
  *G01N 33/00* (2006.01)
  *G01N 21/31* (2006.01)

(52) U.S. Cl.
  CPC ......... *G01N 21/3151* (2013.01); *G01N 21/33* (2013.01); *G01N 33/0027* (2013.01); *H01L 21/205* (2013.01); *G01N 2021/3155* (2013.01); *G01N 2021/3159* (2013.01); *G01N 2021/3181* (2013.01); *G01N 2201/0627* (2013.01); *G01N 2201/0696* (2013.01); *G01N 2201/12* (2013.01)

(58) Field of Classification Search
  USPC ........................................ 250/222.2
  See application file for complete search history.

(56) References Cited

U.S. PATENT DOCUMENTS

| | | | | |
|---|---|---|---|---|
| 5,015,099 | A * | 5/1991 | Nagai | G01N 21/39 250/338.5 |
| 2009/0078860 | A1 | 3/2009 | Kischkat et al. | |
| 2010/0108154 | A1 | 5/2010 | Minami et al. | |
| 2017/0254743 | A1 * | 9/2017 | Sugawa | A61B 5/14532 |
| 2017/0254746 | A1 * | 9/2017 | Sugawa | A61B 5/14532 |

FOREIGN PATENT DOCUMENTS

| | | |
|---|---|---|
| JP | 51-127786 | 11/1976 |
| JP | S564036 | 1/1981 |
| JP | H03-181845 | 8/1991 |
| JP | H04-151546 | 5/1992 |
| JP | 2000-230900 | 8/2000 |
| JP | 3124376 | 10/2000 |
| JP | 2006-324532 | 11/2006 |
| JP | 2010-109304 | 5/2010 |
| JP | 2012-138407 | 7/2012 |
| JP | 2012-211024 | 11/2012 |

* cited by examiner

[Fig. 1]
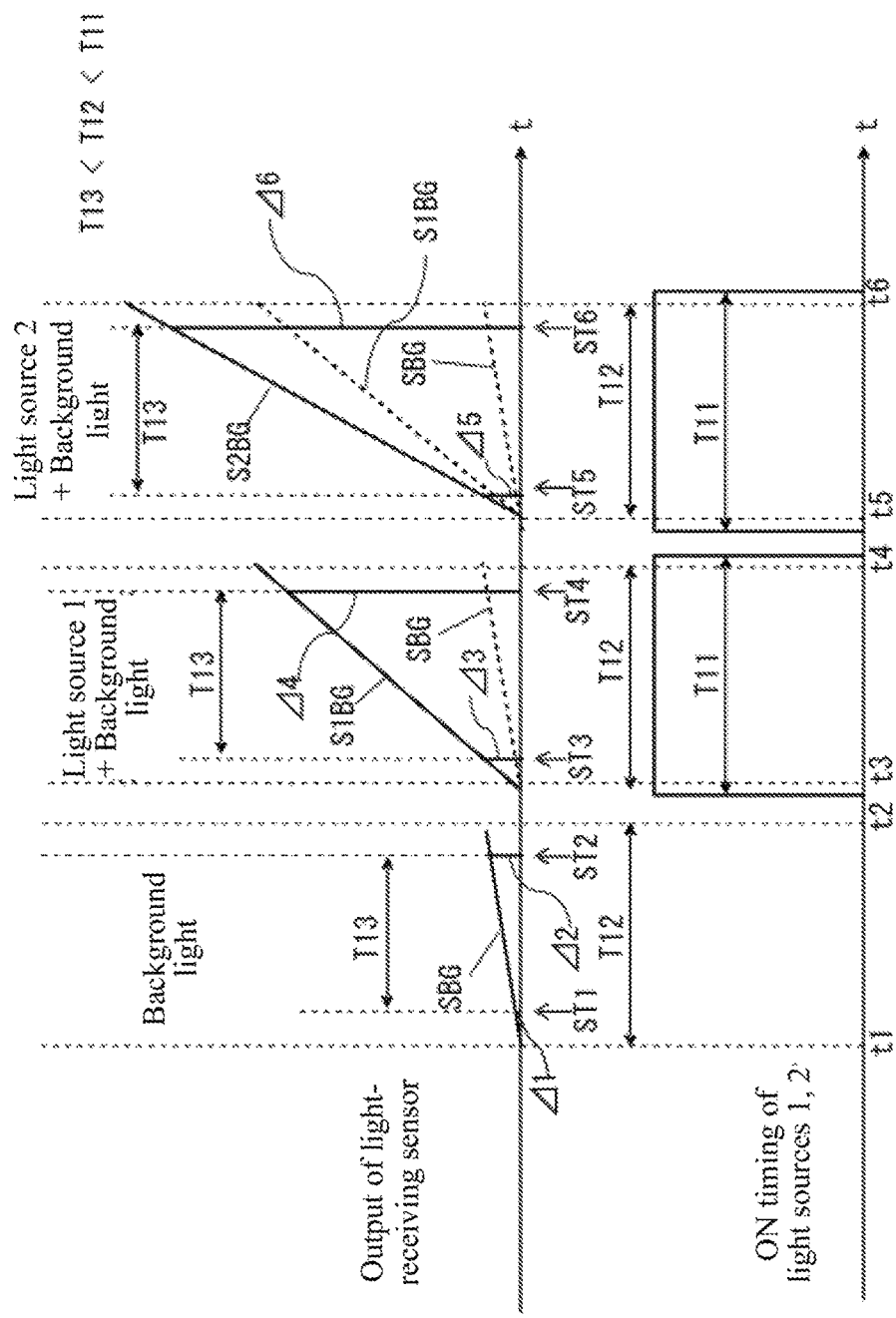

[Fig. 2]
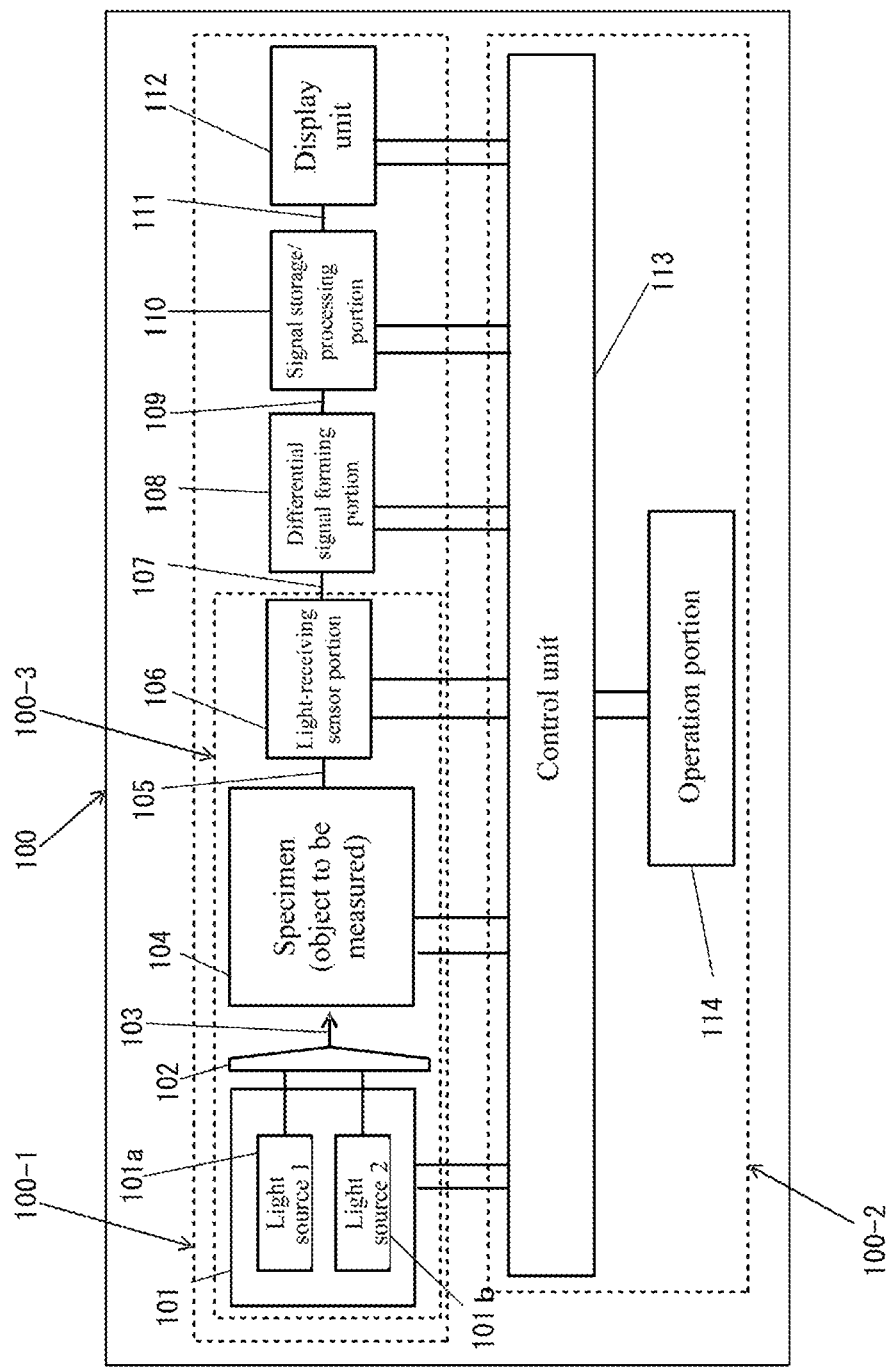

[Fig. 3]
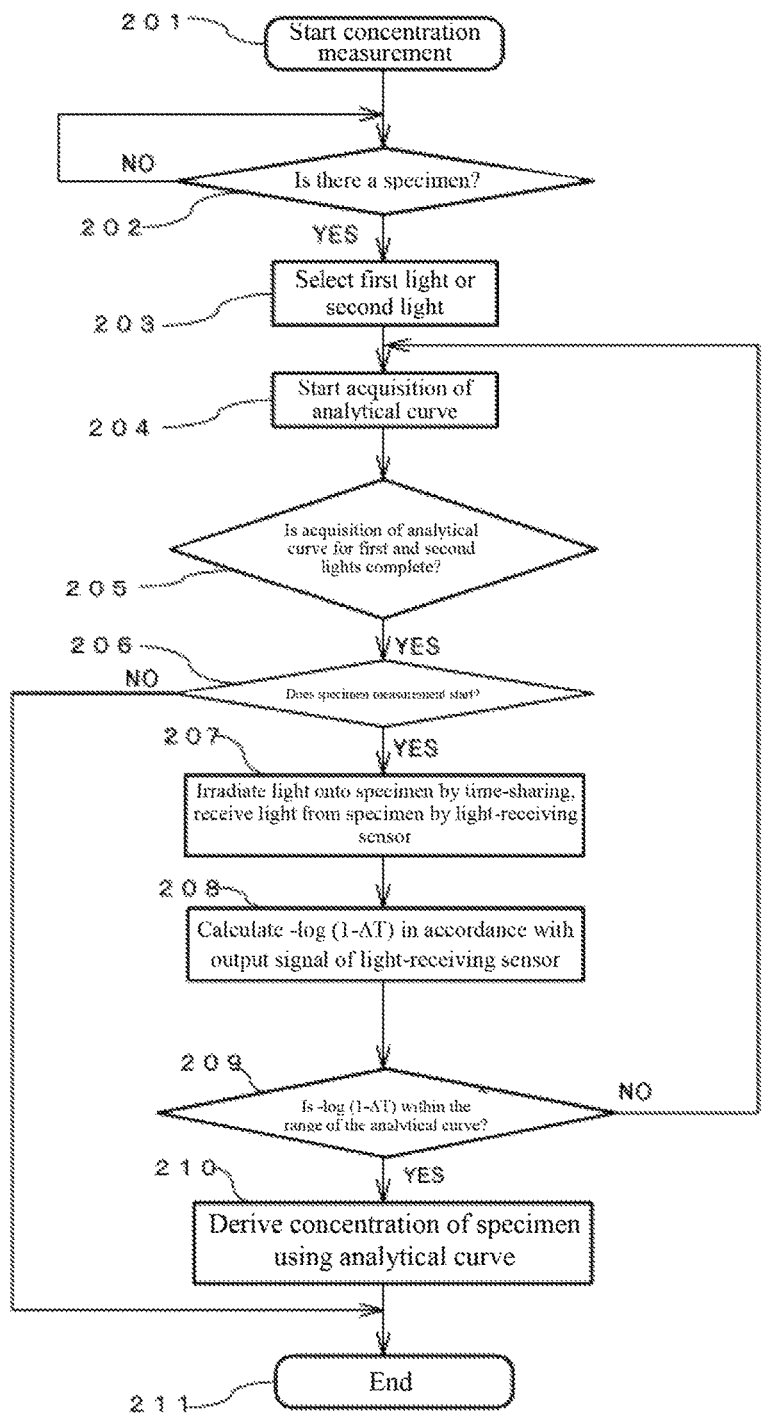

[Fig. 4]
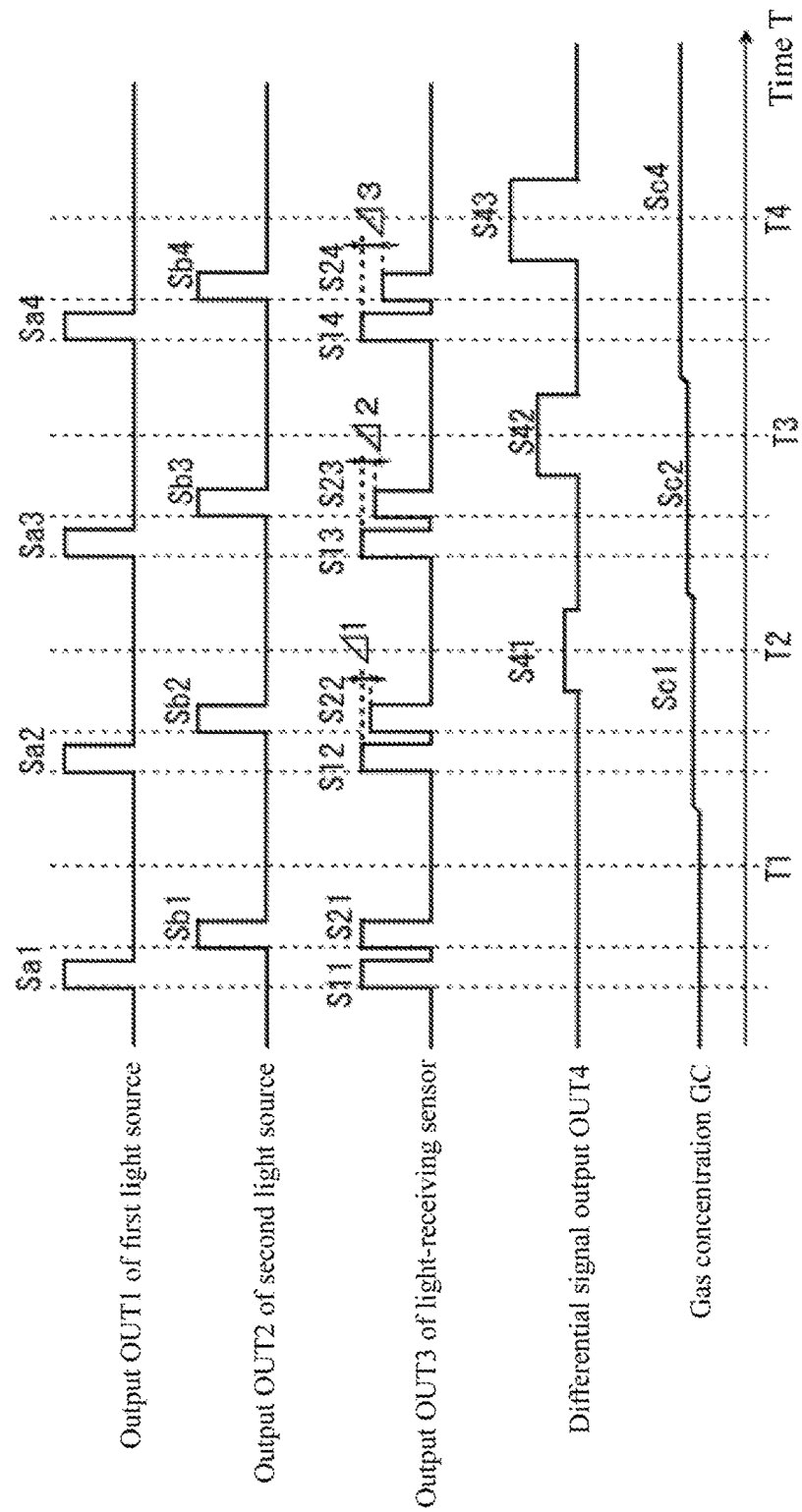

[Fig. 5]
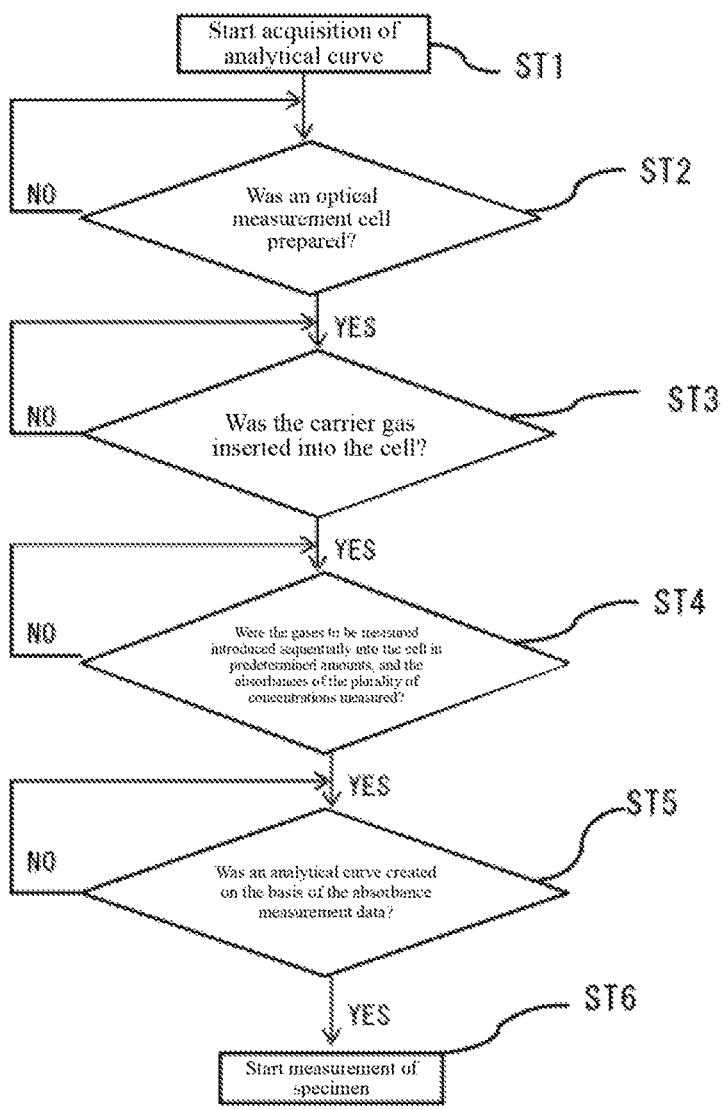

[Fig. 6]
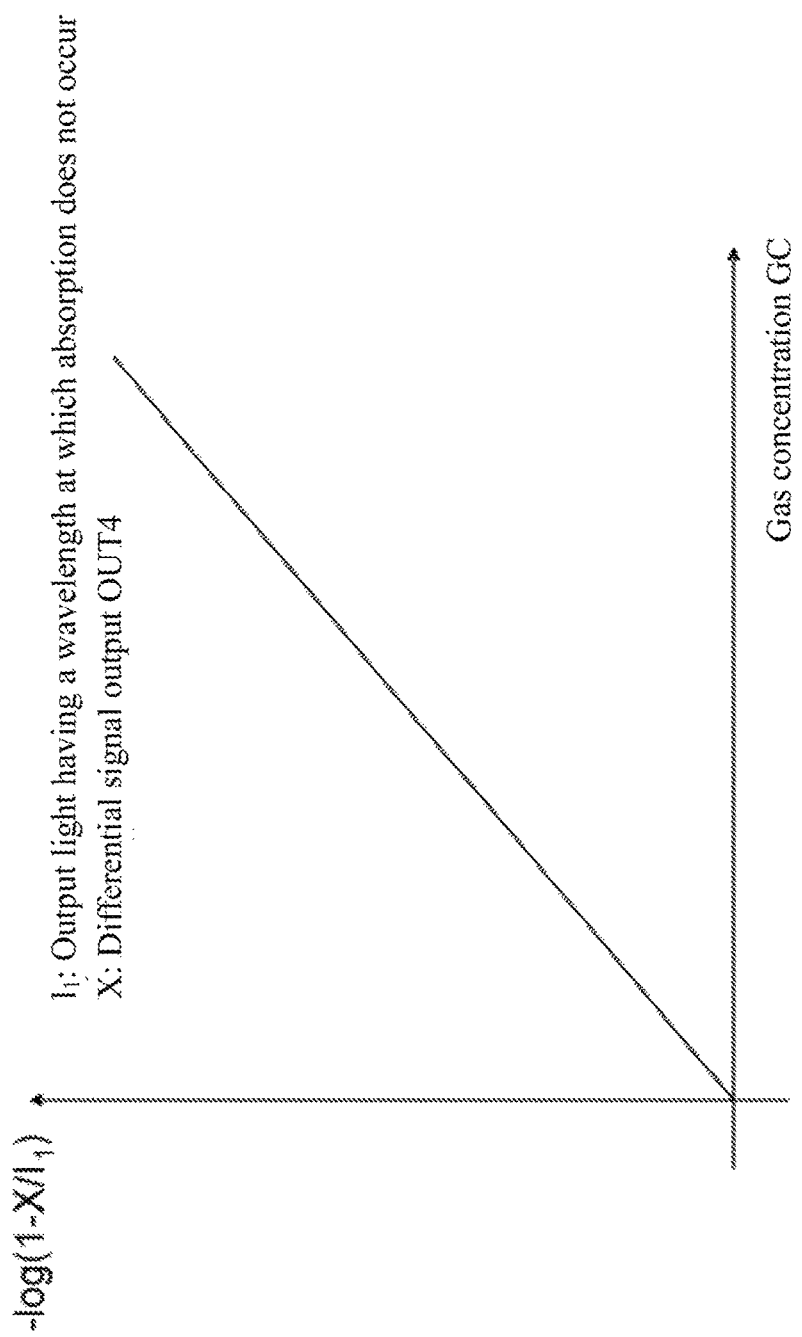

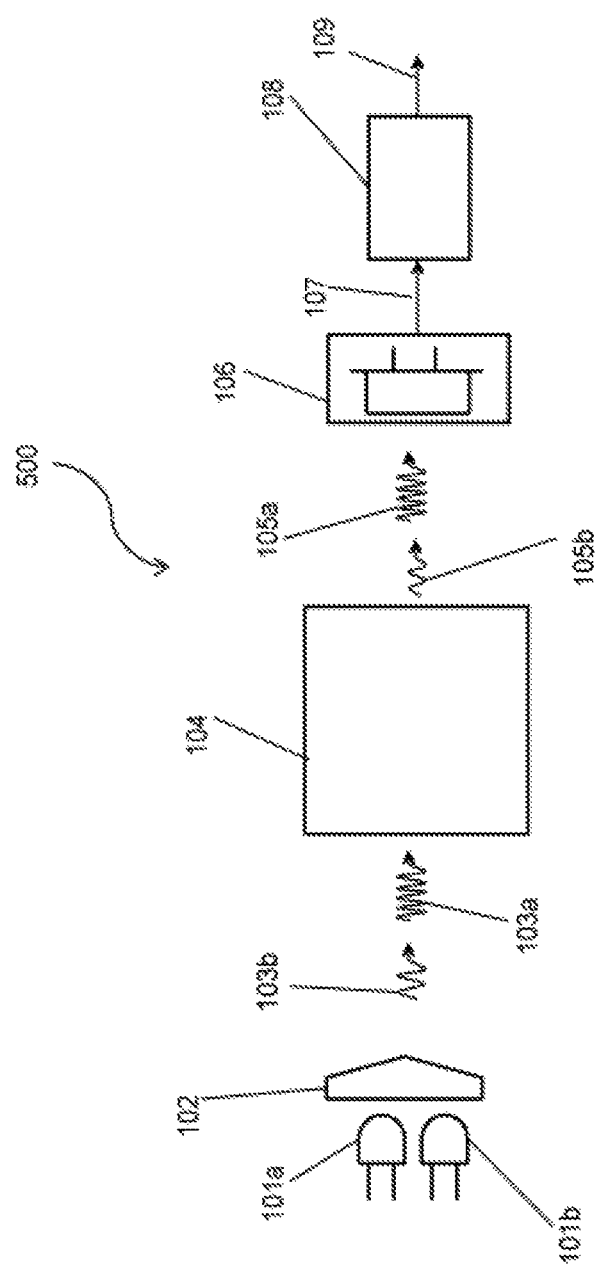
[Fig. 7]

[Fig. 8]
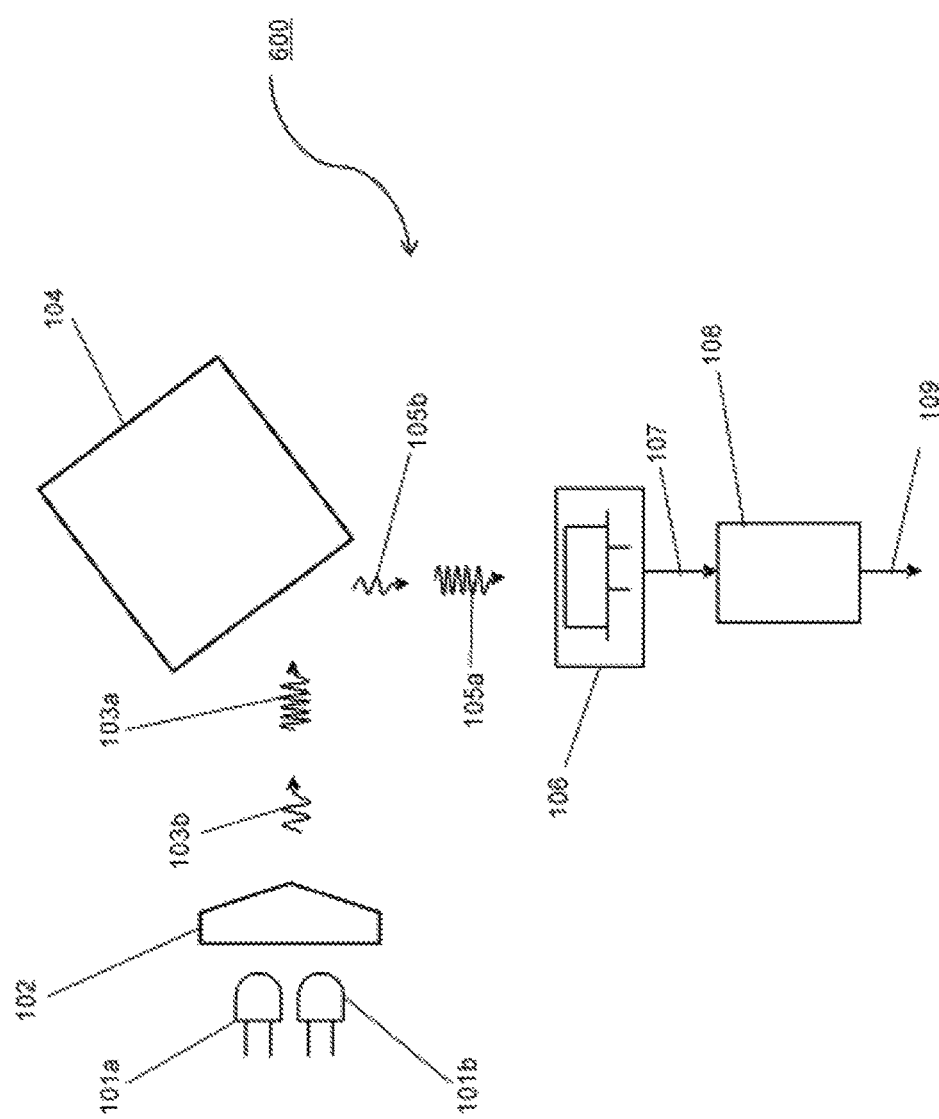

[Fig. 9]
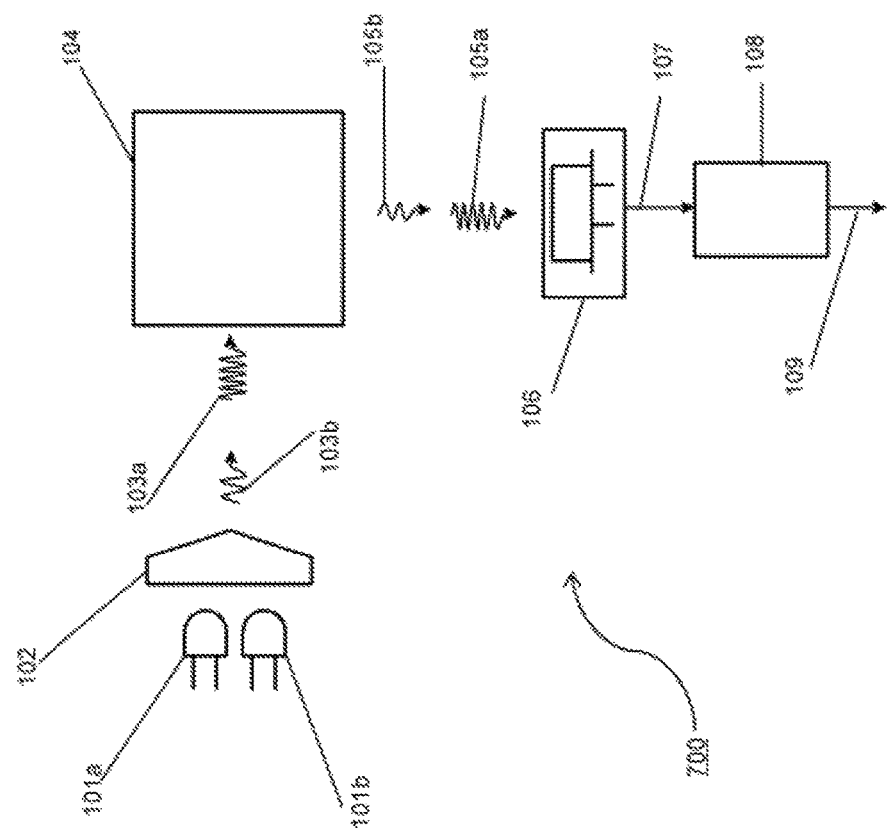

[Fig. 10]
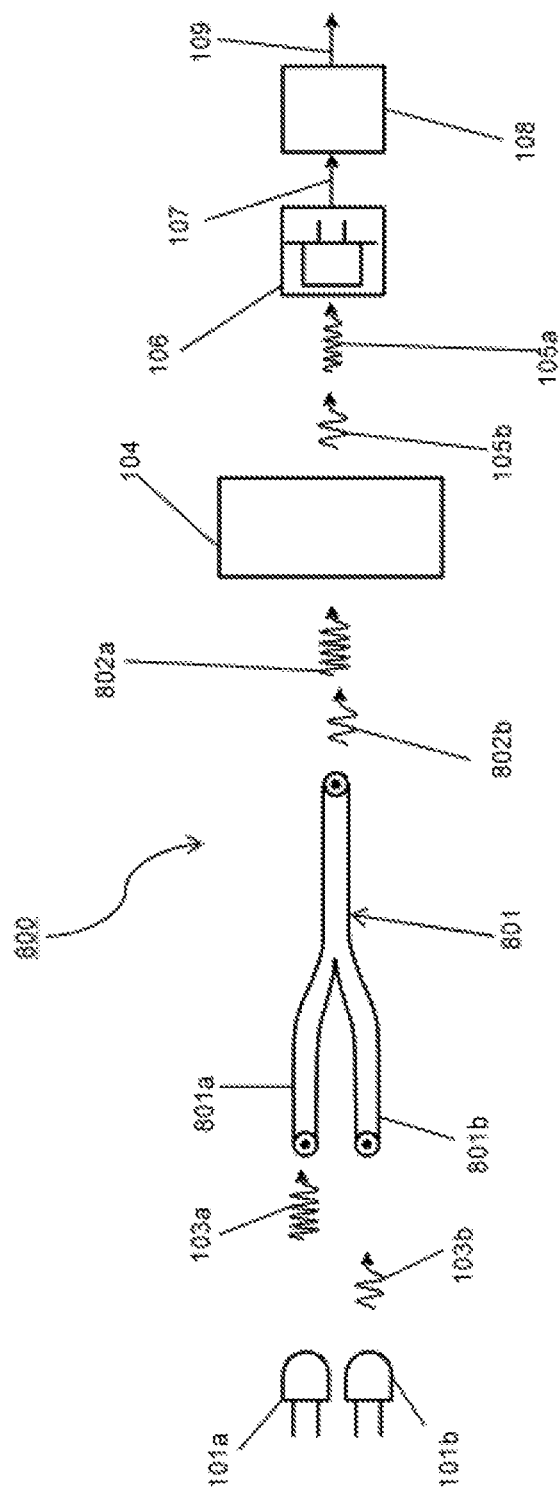

[Fig. 11]
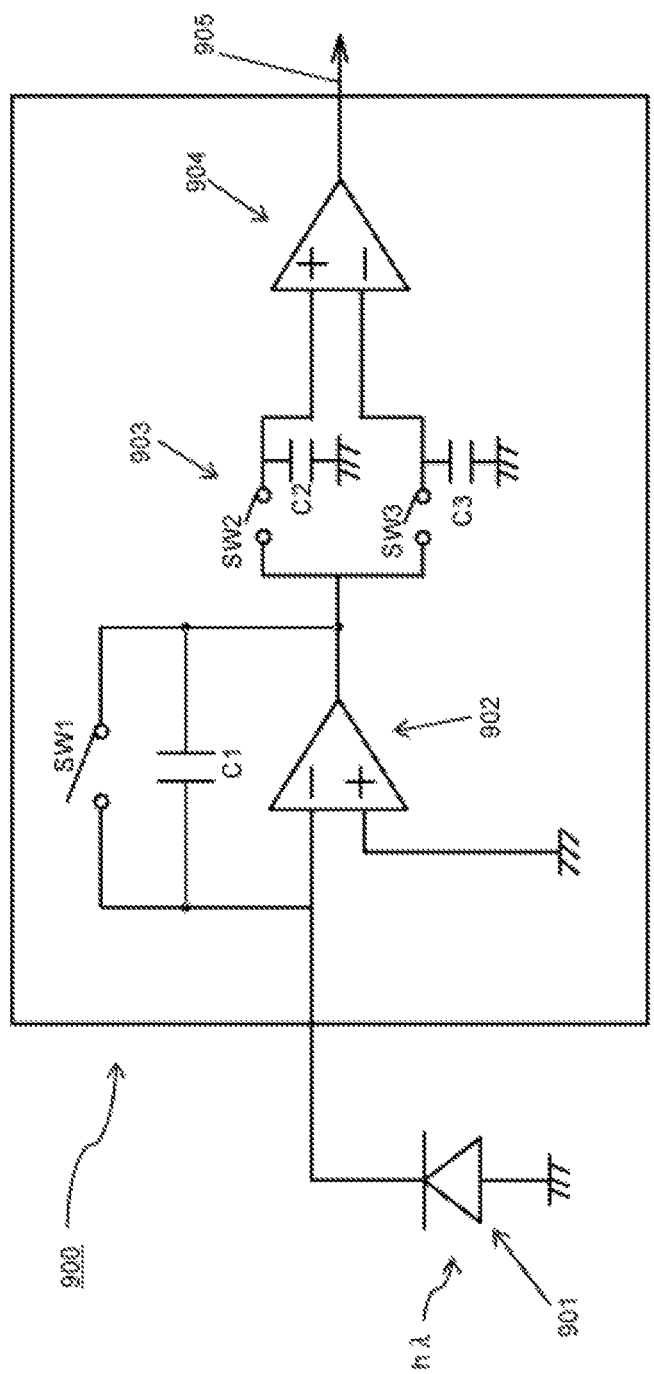

[Fig. 12]
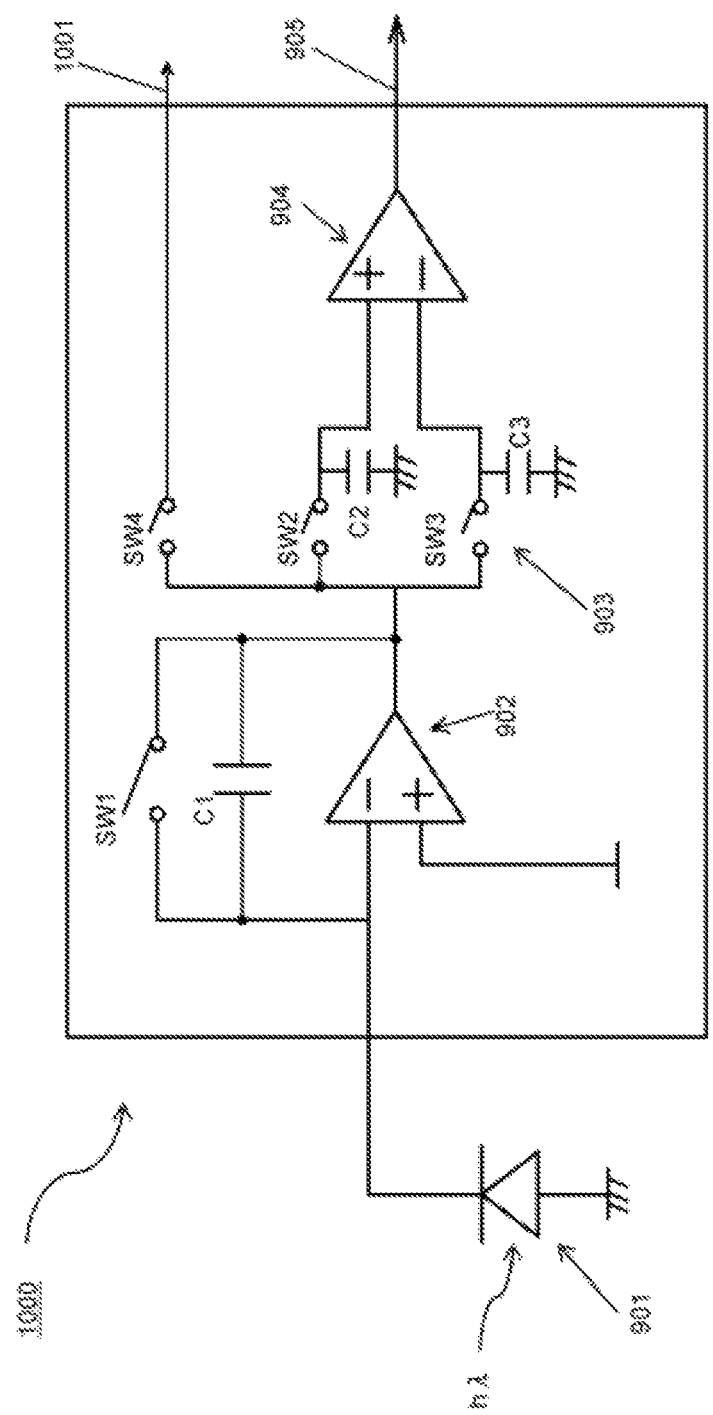

[Fig. 13]
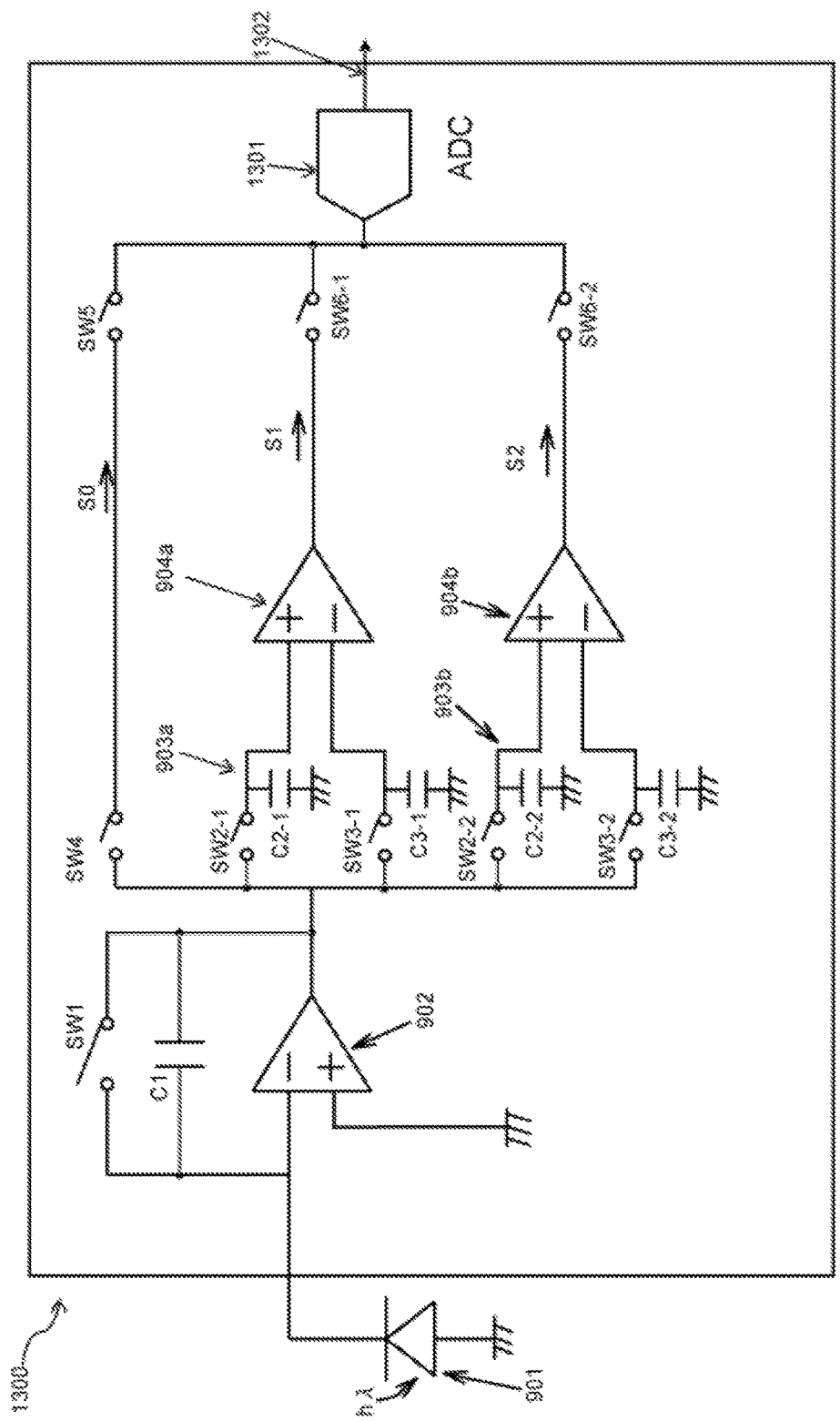

[Fig. 14]
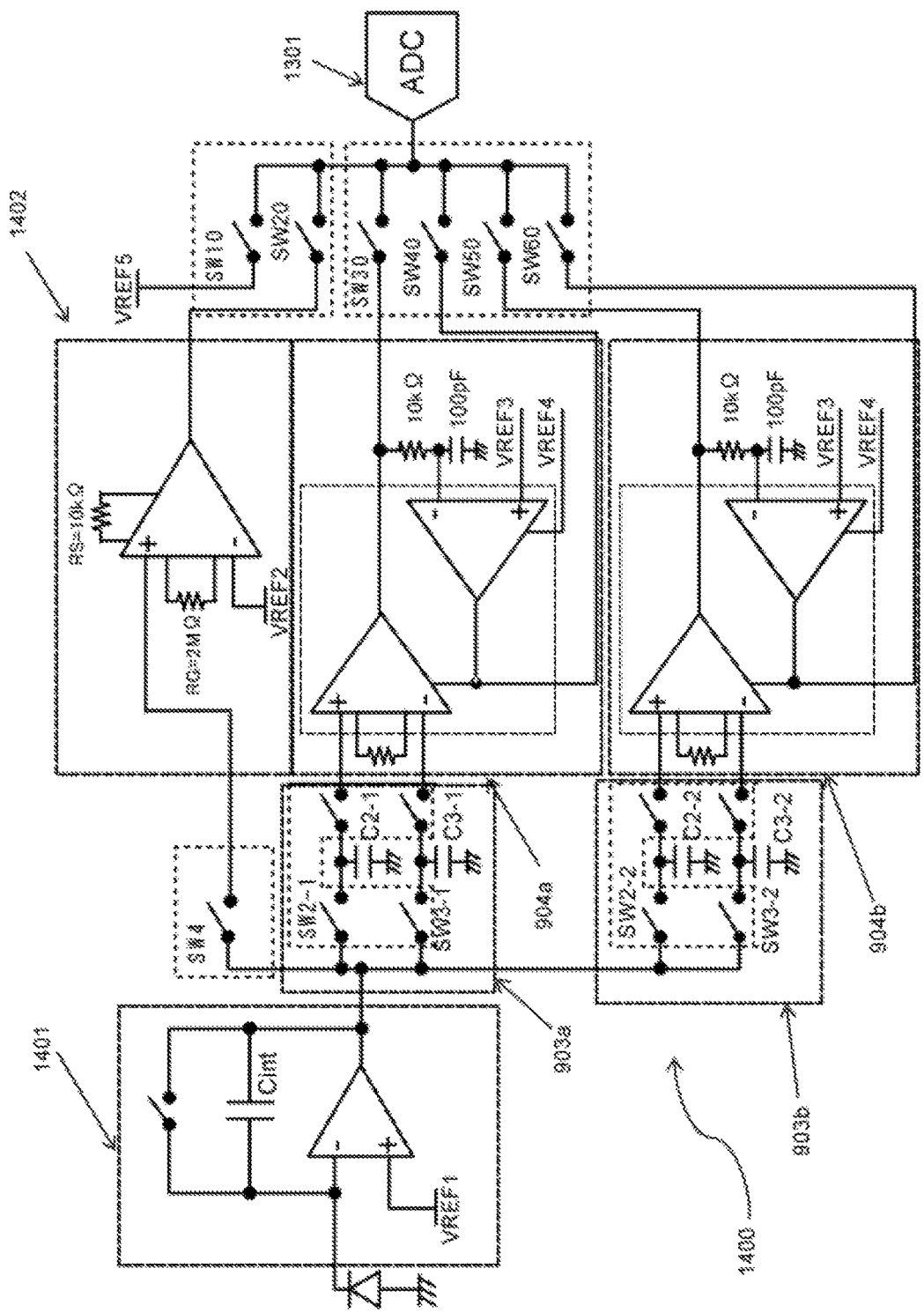

[Fig. 15]
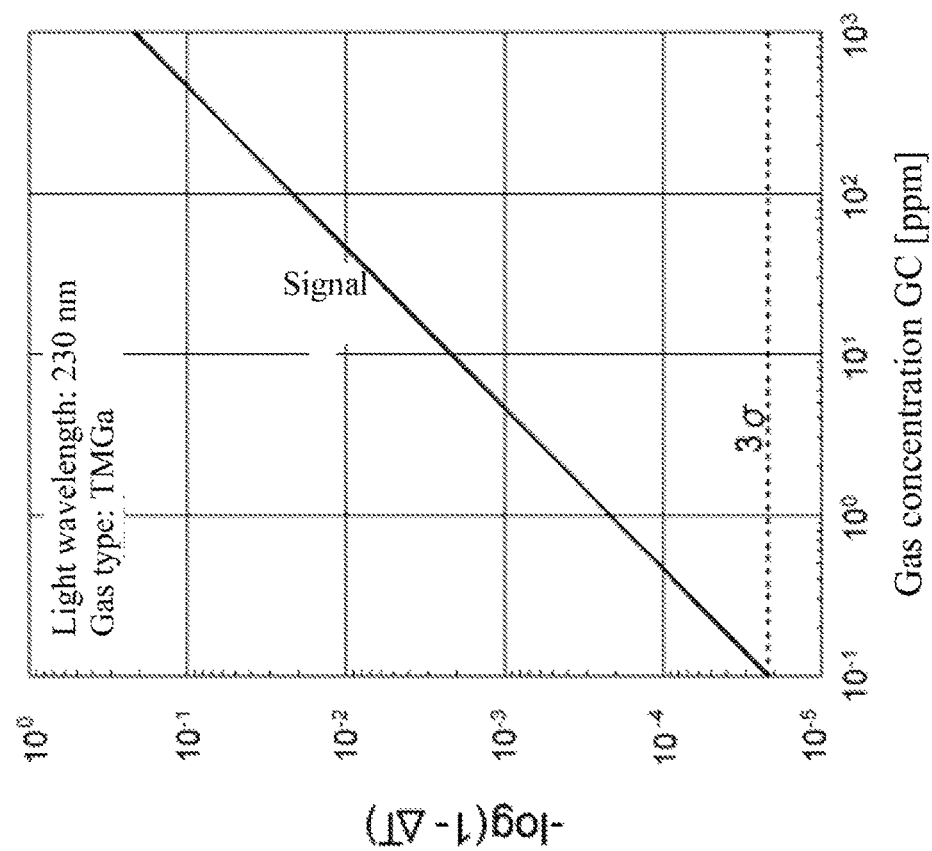

[Fig. 16]
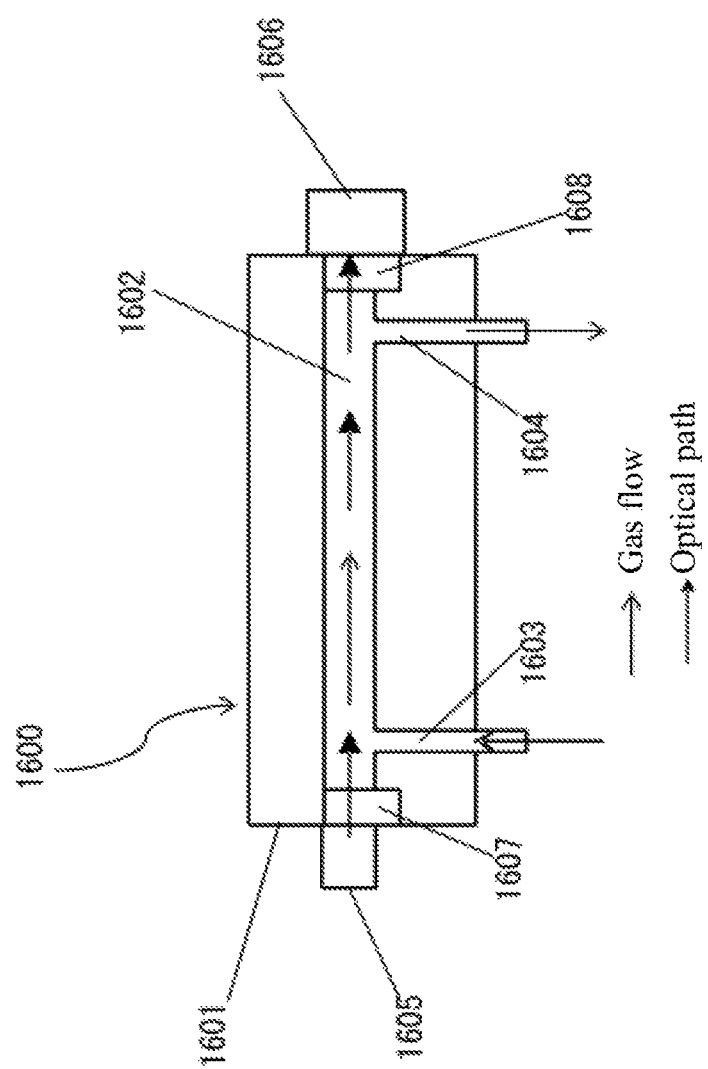

[Fig. 17]
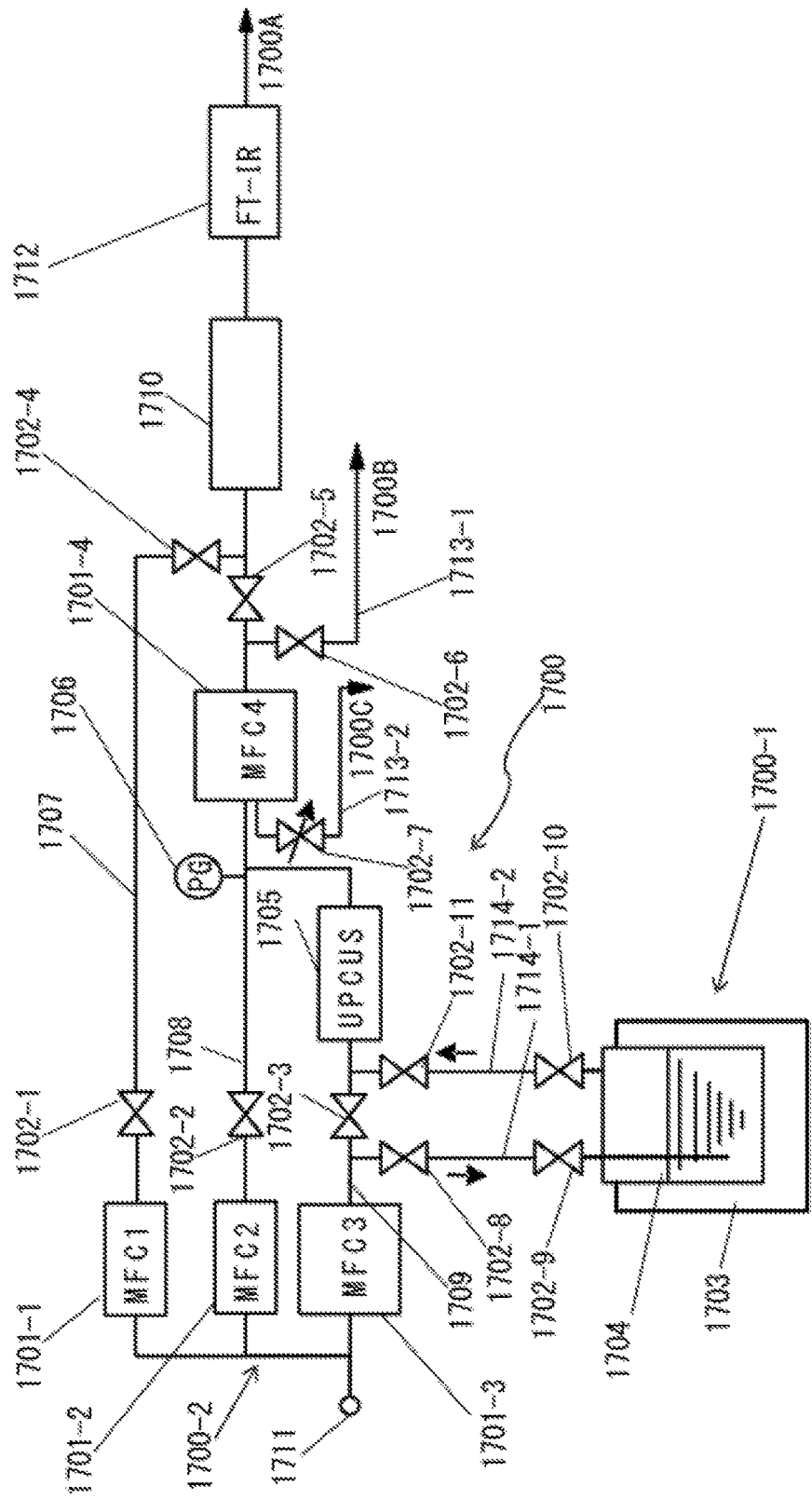

[Fig. 18]
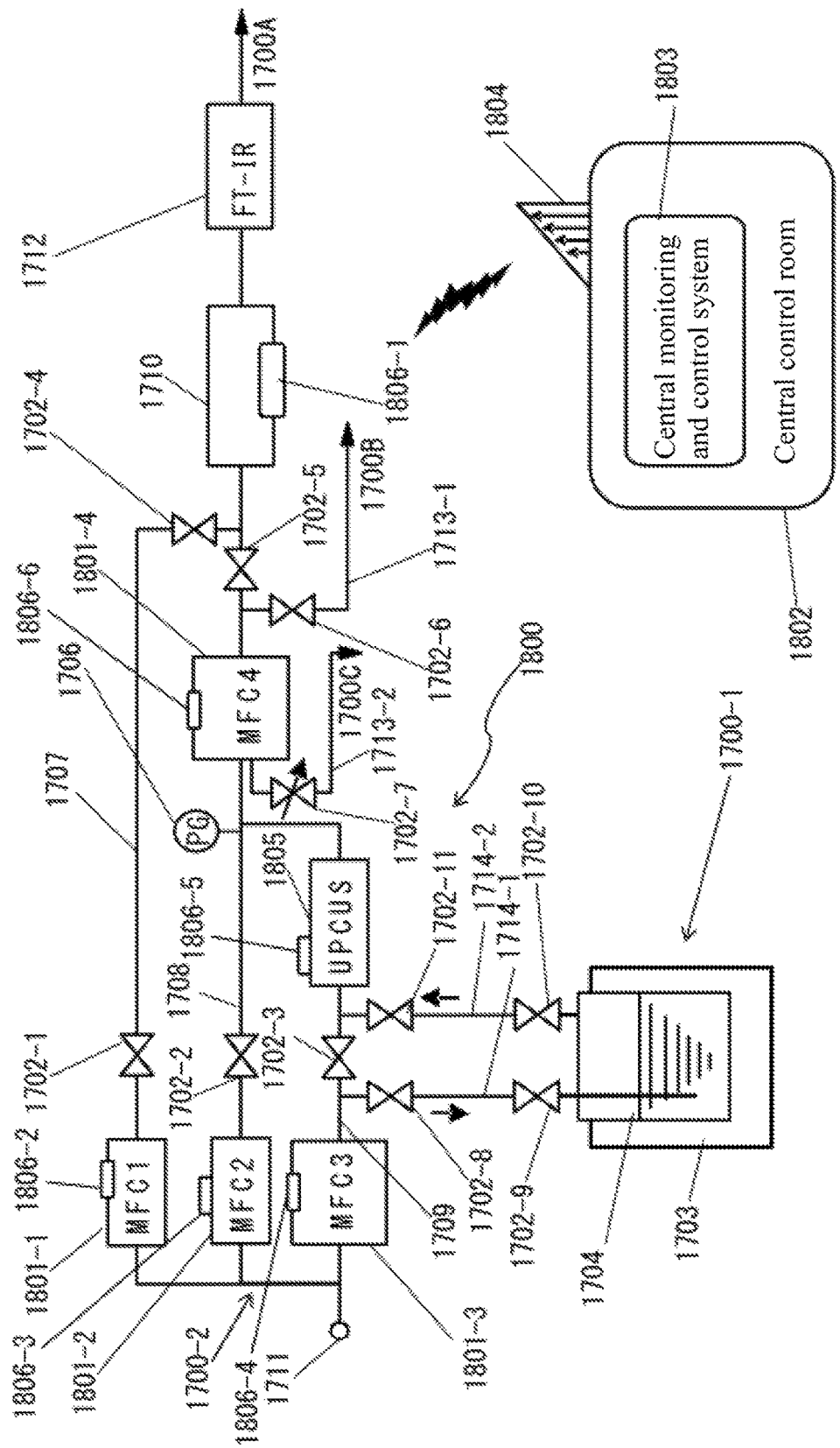

OPTICAL GAS CONCENTRATION MEASURING METHOD BY FORMING A DIFFERENTIAL SIGNAL USING LIGHTS WITH DIFFERENT ABSORBABILITIES TO A RAW MATERIAL IN A GAS FLOW PATH USING A TIME-SHARING METHOD

This application is a national phase of PCT Application No. PCT/JP2015/082742 filed Nov. 20, 2015, which in turn claims benefit of Japanese Application No. 2014-237220 filed Nov. 23, 2014.

BACKGROUND OF THE INVENTION

Field of the Invention

The present invention relates to an optical gas concentration measuring method related to the concentration of a predetermined chemical component in a gas, and a method for monitoring the gas concentration by the method.

Description of the Background Art

In the manufacture of a semiconductor, mixed gases are often supplied from the same line inside a processing chamber of a semiconductor manufacturing device. The supply of such a mixed gas requires that a mixture ratio of component gases be kept constant during the treatment process period, and instantaneously changed as intended. To this end, a flow rate control device, such as a flow control system component (FCSC), for example, that comprises a gas flow rate measurement mechanism and a gas flow rate adjustment mechanism is arranged in the gas supply line. In this FCSC, the degree to which the flow rate per unit time (hereinafter also referred to as "unit flow rate") of each component gas that constitutes the mixed gas can be accurately measured is important.

Today, in a semiconductor manufacturing process in which there are many opportunities to implement a treatment process such as film formation or etching at an atomic- to nano-order level, the unit flow rate of each component gas in a mixed gas immediately prior to introduction to a processing chamber needs to be measured accurately and instantaneously down to a small range.

In a conventional flow rate control device, generally the flow rate of a single component gas prior to mixture is measured and the target mixture ratio of the mixed gas is calculated from the measured flow rate value.

Nevertheless, the mixture ratio of the mixed gas at the moment of introduction into the processing chamber (hereinafter also referred to as "actual mixture ratio") is not always guaranteed to be the same as the mixture ratio calculated from the measured flow rate values (hereinafter also referred to as "measured mixture ratio") during process execution. Thus, conventionally a feedback mechanism is provided that measures the flow rate of each single component gas either continually or at a predetermined interval, and adjusts each of the flow rates so that, when the flow rate of any single component gases fluctuates, the mixture ratio becomes the original predetermined mixture ratio based on the new value (Patent Document 1, for example).

On the other hand, examples of a gas concentration measuring system include a system that uses a partial pressure measurement sensor that measures the partial pressure of a material gas by a non-dispersive infrared absorption method, and calculates the concentration of the material gas on the basis of the partial pressure measurement value of this sensor by a mathematical operation (Patent Document 2, for example).

Further, in metal organic compound chemical vapor deposition (MOCVD; chemical vapor deposition that uses a metal organic compound) as well, formation of a uniform film requires control of the supplied concentration of the metal organic compound so that the supplied concentration of the metal organic compound is constant during the film formation process period, or so that the supplied concentration fluctuates in accordance with the component distribution of the metal organic compound to ensure formation of a film with a preferred component distribution. Generally, the metal organic compound is mixed into a carrier gas via bubbling or the like, and supplied to the processing chamber. The used metal organic compound is not limited to a single compound, and a plurality of compounds may be used as well. Examples of the method used to supply the raw material gases of a plurality of types of metal organic compounds in accordance with design values include a method for using infrared gas analysis means (Patent Document 3, for example).

Further, in a system in which bubbling is used, problems such as the following also arise (Patent Document 4).

During film formation, a predetermined number of organic metal gases are supplied from a secondary side of each of a plurality of bubbling vessels to a switch valve, the organic metal gases combined by the switching of the switch valve are supplied to a reactor, and the film is formed.

For example, during InGaP film formation, organic metal supply lines, such as a trimethylindium (TMI) supply line, a trimethylgallium (TMG) supply line, a phosphine ($PH_3$) supply line, and an arsine ($AsH_3$) supply line, supply organic metals to the reactor, and a film is formed by a metal organic chemical vapor deposition (MOCVD) method.

In a semiconductor laser of a compound semiconductor (for GaAs substrate usage), an LED, or the like, a multilayered film is formed using an MOCVD method. When a multilayered film is formed by a conventional vapor deposition device of a compound semiconductor, a certain film layer is formed and then the organic metal gases for the next film formation are supplied to the reactor by opening and closing a plurality of switch valves. When a valve is opened, however, the flow rate to the reactor suddenly becomes excessively high, resulting in the occurrence of time delays until stabilization to a specified flow rate, adversely affecting the consistency of the formed film thicknesses.

In addition, to ensure that the internal pressure of the reactor is constant, the total flow rate inside the reactor must be constant during film formation. That is, when the internal pressure of the reactor is not constant, fluctuation in internal pressure causes inconsistencies in film thickness. As a result, while the organic metal gases are supplied at specified flow rates during film formation of a certain layer, a carrier gas for flow rate compensation is supplied at a required rate by a mass flow controller when the flow rate does not satisfy a predetermined total flow rate inside the reactor.

Nevertheless, while the flow rate of the carrier gas for flow rate compensation changes when the specified flow rate of an organic metal gas differs from that during all film formations, the flow rate change performed by the mass flow controller may incur a time delay until the flow rate stabilizes at the new value, resulting in a time delay until the internal pressure of the reactor becomes constant, thereby adversely affecting the consistency of film formation. The time delay until the compensatory carrier gas flow rate reaches a constant flow rate may cause an abruptness between film formations to worsen, adversely affecting the characteristics of the produced semiconductor.

PATENT DOCUMENTS

Patent Document 1: Japanese Laid-Open Patent Application No. 2012-138407
Patent Document 2: Japanese Laid-Open Patent Application No. 2010-109304
Patent Document 3: Japanese Laid-Open Patent Application No. 2006-324532
Patent Document 4: Japanese Patent No. 3124376

SUMMARY OF THE INVENTION

Problems to be Solved by the Invention

In the concentration measuring method or concentration adjustment method set forth in each of the patent documents described above, problems such as the following exist.

In Patent Document 1, the flow rate is measured on an upstream side of the processing chamber and merely fed back, and thus the problem of whether or not the measured mixture ratio and actual mixture ratio are identical remains unresolved. Furthermore, while the length of the supply line from the mixing position to the position of introduction into the processing chamber needs to be adequately set to ensure that the mixed state of the gases is uniform, doing so makes it all the more difficult to regard the measured mixture ratio and actual mixture ratio as identical. To ensure that the measured mixture ratio and the actual mixture ratio are identical, one may consider positioning the mixing position and the introduction position as close to each other as possible, but doing so results in the problem that it is difficult to guarantee a uniform mixture. Attempting to resolve such problems in addition to the problems described above results in an increasingly complex mechanism, and requires rather advanced control technology. Additionally, according to the configuration of Patent Document 1, measurement is performed by flow rate measurement, and thus gases cannot be specified.

In the case of Patent Document 2, measurement is performed by partial pressure measurement and thus the method is unsuitable for such high accuracy measurement as addressed here. Furthermore, the measurement error undeniably increases when the partial pressure measurement is performed in a range of an extremely small order.

The method disclosed in Patent Document 3 is configured to individually adjust any one of first infrared gas analysis means for measuring the concentration of each raw material gas in a mixed gas supplied from a gas mixing chamber to a reaction chamber, second infrared gas analysis means for measuring a concentration of each raw material gas in a discharged gas discharged from the reaction chamber, the flow rate control means for calculating an amount of consumption of each raw material gas inside the reaction chamber based on the measurement results of the first and second infrared gas analysis means and setting the difference between the calculated value and a predetermined design value as a control amount, a gas supply source temperature control unit, and a substrate temperature control unit. Thus, the raw material gases consumed not by film formation but by an inner wall surface of the reaction chamber and the like are not taken into consideration, making it difficult to form a thin film having a uniform film thickness and uniform components. Moreover, a specific example of the infrared gas analysis means is not illustrated in Patent Document 3.

As a result, while formation of a thin film having uniform components and a uniform film thickness at the nano-order level requires strict control of the supplied concentration of the metal organic compound in order to supply the metal organic compound to the processing chamber at a predetermined concentration for a certain period of time, demanding high accuracy in concentration measurement, this demand is not simply satisfied.

As understood from the above description, a gas concentration measuring method that allows quick and accurate measurement of a concentration of a predetermined chemical component in a gas atmosphere down to an extremely small concentration range in a non-destructive manner using simple means has not yet been provided.

Further, a gas concentration measuring method that allows measurement of the concentrations of a plurality of chemical components in an object to be measured (gas atmosphere) with high accuracy in real time using the same measurement system and the same conditions has not yet been provided.

Furthermore, a gas concentration measuring method that allows quick and accurate measurement of the concentration of a chemical component in an object to be measured down to an extremely small concentration range in the nano order in real time, the method having universality, i.e., the ability to be embodied in various forms and modes, has not yet been provided.

Furthermore, a gas concentration measuring method that allows quick and accurate measurement of the concentrations of a plurality of chemical components in an object to be measured in real time using a simple configuration has not yet been provided.

The present invention was achieved as a result of close research on the points described above, and it is therefore an object of the present invention to provide a gas concentration measuring method that allows quick and accurate measurement of a gas concentration of a chemical component to be measured in real time, using a simple configuration, and a method for monitoring a gas concentration by the method.

Another object of the present invention is to provide a gas concentration measuring method that allows quick and accurate measurement of a gas concentration of a chemical component in an object to be measured, down to an extremely small concentration range in the nano order in real time using a simple configuration, the method having universality, i.e., the ability to be embodied in various forms and modes, and a method for monitoring a gas concentration by the method.

Yet another object of the present invention is to provide a gas concentration measuring method that allows quick and accurate measurement of a gas concentration of a chemical component to be measured in a non-destructive, non-contact manner, down to an extremely small range using a simple configuration, and a method for monitoring a gas concentration by the method.

Yet another object of the present invention is to provide a gas concentration measuring method that allows measurement of a gas concentration of a chemical component to be measured, down to an extremely small range, with measurement errors based on environmental fluctuations and characteristic fluctuations of system components, such as electrical circuits or electronic elements, eliminated at least to the extent substantially possible, and a method for monitoring a gas concentration by the method.

Yet another object of the present invention is to provide a gas concentration measuring method that allows quick and accurate measurement of gas concentrations of a plurality of chemical components to be measured in an object to be measured in real time, on a per component basis, using a simple configuration, and a method for monitoring a gas concentration by the method.

Means for Solving the Problems

A first aspect of the present invention is an optical gas concentration measuring method when a chemical process or a physical process is to be implemented upon introduction of a raw material gas into a processing chamber from a gas supply line in which optical gas concentration measurement means comprising a gas flow path is arranged in a predetermined position, the method comprising the steps of irradiating light having a first wavelength that has an absorbability with respect to the raw material gas, and light having a second wavelength that has no or substantially no absorbability with respect to the raw material gas, or an absorbability that is relatively lower than that of the light having the first wavelength, along the same or substantially the same optical path and onto the raw material gas in the gas flow path using a time-sharing method; receiving a first exiting light on the basis of the light having the first wavelength and a second exiting light on the basis of the light having the second wavelength, the first exiting light and the second exiting light exiting from the optical path, in a photodetector disposed on an end edge of the optical path; inputting a first differential circuit input signal in accordance with a first signal based on the first exiting light, and a second differential circuit input signal in accordance with a second signal based on the second exiting light, the first signal and the second signal being output by the photodetector according to the received light, into a differential circuit; and comparing a measured value that is based on an output signal output from the differential circuit in accordance with the input, with data stored in advance in storage means to derive a concentration of the raw material gas.

A second aspect of the present invention is an optical gas concentration measuring method when a chemical process or a physical process is to be implemented upon introduction of a raw material gas into a processing chamber from a gas supply line in which optical gas concentration measurement means comprising a gas flow path is arranged in a predetermined position, the method comprising the steps of: irradiating light having the first wavelength and light having the second wavelength, each having a different light absorptivity with respect to the raw material gas, onto the raw material gas in the gas flow path using a time-sharing method; receiving the light of each wavelength that optically passes through the raw material gas according to the irradiation of the light of each wavelength, using a common light-receiving sensor; forming a differential signal between a first related to the light having the first wavelength and a signal related to the light having the second wavelength output from the light-receiving sensor in accordance with the received light; and deriving a concentration of a chemical component of the object to be measured on the basis of the differential signal.

Effect of the Invention

According to the present invention, it is possible to measure a concentration of a predetermined chemical component (gas component) quickly and accurately in a non-destructive manner down to an extremely small concentration range using simple means.

Further, it is possible to measure with high accuracy the concentrations of a plurality of chemical components in an object to be measured (gas atmosphere) in real time using the same measurement system and the same conditions.

Furthermore, it is possible to provide a gas concentration measuring method that allows quick and accurate measurement of a concentration of a chemical component in an object to be measured, down to an extremely small concentration range in the nano order in real time, the method having universality, i.e., the ability to be embodied in various forms and modes.

BRIEF DESCRIPTION OF THE DRAWINGS

FIG. 1 is a timing chart for explaining the principles of an optical gas concentration measuring method according to the present invention.

FIG. 2 is a block diagram for explaining a configuration of a preferred embodiment of an optical gas concentration measuring system that embodies the optical gas concentration measuring method according to the present invention.

FIG. 3 is a flowchart for explaining a preferred embodiment of the optical gas concentration measuring method according to the present invention.

FIG. 4 is a timing chart for explaining a signal output timing of the example in FIG. 3.

FIG. 5 is a flowchart for finding an analytical curve.

FIG. 6 is a graph showing a relationship between a gas concentration GC and "$-\log (1-\Delta T)$."

FIG. 7 is an explanatory schematic configuration view for explaining a main component of a preferred embodiment of the optical gas concentration measuring system that embodies the optical gas concentration measuring method according to the present invention.

FIG. 8 is an explanatory schematic configuration view for explaining main components of another preferred embodiment of the optical gas concentration measuring system that embodies the optical gas concentration measuring method according to the present invention.

FIG. 9 is an explanatory schematic configuration view for explaining main components of yet another preferred embodiment of the optical gas concentration measuring system that embodies the optical gas concentration measuring method according to the present invention.

FIG. 10 is an explanatory schematic configuration view for explaining a main component of yet another preferred embodiment of the optical gas concentration measuring system that embodies the optical gas concentration measuring method according to the present invention.

FIG. 11 is a circuit diagram for explaining a preferred example of a differential signal forming portion adopted in the present invention.

FIG. 12 is a circuit diagram for explaining another preferred example of the differential signal forming portion adopted in the present invention.

FIG. 13 is a circuit diagram for explaining yet another preferred example of the differential signal forming portion adopted in the present invention.

FIG. 14 is a circuit diagram for explaining yet another preferred example of the differential signal forming portion adopted in the present invention.

FIG. 15 is a graph showing a relationship between an absorbance value measured with respect to a gas concentration and a value equivalent to three times a standard deviation of a noise superimposed on the measured signal.

FIG. 16 is an explanatory schematic configuration view for explaining an outline of main components of a gas concentration measuring portion of the gas concentration measuring device according to the present invention.

FIG. 17 is a schematic configuration view for explaining a preferred example of a measuring system that measures a gas concentration by applying the gas concentration measuring method of the present invention.

FIG. 18 is a schematic configuration view for explaining a preferred example of a production line of an electronic device to which the gas concentration measuring method of the present invention is applied.

DESCRIPTION OF THE PREFERRED EMBODIMENTS

FIG. 1 is a timing chart for explaining the principles of an optical gas concentration measuring method according to the present invention.

In FIG. 18, light sources 1, 2 are regularly turned ON and OFF at a pulse width T11 (ON time) as illustrated (the pulse width T11 is the pulse width of a light source ON pulse PL that turns ON the light sources 1, 2).

A light-receiving sensor is regularly turned ON at a pulse width T12 (the time during which the light-receiving sensor receives light and an output signal corresponding to the amount of received light is output) as illustrated (the pulse width T12 is the pulse width of a sensor drive pulse SP that drives the light-receiving sensor ON and OFF).

While the ON/OFF timing of the sensor drive pulse SP is within the pulse width 11 of the light source ON pulse PL in FIG. 18, the present invention is not limited thereto. That is, the ON/OFF timing of the sensor drive pulse SP may be the same as the ON/OFF timing of the light source ON pulse PL.

The relationship of T11, T12, T13, when expressed in a formula, is as follows.

$$T13 < T12 \leq T11 \quad (1)$$

When the sensor drive pulse SP turns ON, the (photo-)charge produced by the light that entered the light-receiving sensor in the ON state is stored in an integrating amplifier or storage capacitance provided in a latter stage of the light-receiving sensor. The change over time of the stored charge amount by this charge storage is indicated by a signal SBG (background light only), a signal S1BG (light source 1+background light), and a signal S2BG (light source 2+background light). That is, timings t1, t3, t5 are the input start timings of signals from the light-receiving sensor to the integrating amplifier or storage capacitance described above, and timings t2, t4, t6 are the input end timings of signals from the light-receiving sensor to the integrating amplifier or storage capacitance described above.

Next, the signal readout in the present invention will be described.

In the present invention, an optical gas concentration measuring device for embodying the optical gas concentration measuring method according to the present invention is started, and the signal of the absolute value of the background light in the space where the system is placed can be read as signals Δ1, Δ2 at signal sampling timings ST1, ST2.

When light from the light source 1 that emits light (Lλ1) having a first wavelength is received by the light-receiving sensor, the signal can be read as signals Δ3, Δ4 at signal sampling timings ST3, ST4.

When light from the light source 2 that emits light (Lλ2) having a second wavelength is received by the light-receiving sensor, the signal can be read as signals Δ5, Δ6 at signal sampling timings ST5, ST6.

In the present invention, (Δ6-Δ5) is read as a differential signal, thereby making it possible to obtain a differential signal that is not affected by background light (signal from light source 2−signal from light source 1).

Further, to increase signal readout accuracy, the differential signal may be obtained as:

$$(\Delta 6 - \Delta 5) - (\Delta 4 - \Delta 3): \text{(Signal from light source} \\ 2+\text{background light)} - \text{(Signal from light source} \\ 1+\text{background light)} \quad (2)$$

As described above, according to the present invention, measurement data can be calibrated using the absolute value output X, even if a change occurs in the amount of light of the light source, the absorbance of an object to be measured, or the like, as a result of a temperature change.

With the light-receiving signals from the light sources 1, 2 output as differential output signals, noise of a circuit system can be removed, making it possible to achieve detection with high accuracy, even if the concentration is weak.

FIG. 2 shows a block diagram of a configuration example of an optical gas concentration measuring system 100 serving as a preferred embodiment that embodies the optical gas concentration measuring method according to the present invention.

The optical gas concentration measuring system 100 illustrated in FIG. 2 comprises an optical gas concentration measuring sub-system 100-1 and a control/operation sub-system 100-2.

The optical gas concentration measuring sub-system 100-1 comprises an optical gas concentration measuring device 100-3.

The optical gas concentration measuring sub-system 100-1 comprises a light source portion 101, a light-focusing optical portion 102, a light-receiving sensor portion 106, a differential signal forming portion 108, a signal storage/processing portion 110, and a display unit 112.

The control/operation sub-system 100-2 comprises a control unit 113 and an operation portion 114.

An object 104 to be measured, subject to concentration measurement of a preferred chemical component, is arranged in a predetermined position between the light-focusing optical portion 102 and the light-receiving sensor portion 106 during measurement.

While the light source portion 101 illustrated in FIG. 2 comprises two light sources including a light source 101a that emits the light (Lλ1) having the first wavelength and a light source 101b that emits the light (Lλ2) having the second wavelength, the present invention is not limited thereto, allowing a single light source that emits the light (Lλ1) having the first wavelength and the light (Lλ2) having the second wavelength.

A light-emitting portion capable of irradiating light having two or more different wavelengths such as described above may comprise two or more light-emitting elements, each capable of irradiating light having one type of wavelength. Furthermore, the light-emitting portion preferably comprises at least one light-emitting element (multiple wavelength light-emitting element) capable of Irradiating light having two or more different wavelengths. This decreases the number of light-emitting elements arranged in the device interior, making it possible to reduce the size of the device.

When two light sources are adopted, disposing the two light sources as close to each other as possible so that each light can be irradiated on substantially the same optical axis increases the accuracy of the measured value, and is thus preferred.

When the lights (L$\lambda$1, L$\lambda$2) having the two wavelengths are irradiated using a single light source, the light (L$\lambda$1) and the light (L$\lambda$2) are selectively separated by means such as a wavelength selecting optical filter prior to being irradiated onto the object 104 to be measured.

When the lights (L$\lambda$1, L$\lambda$2) having the two wavelengths are irradiated using a single light source, the device is designed so that the light having the applicable wavelength is irradiated in accordance with an irradiation timing using an optical wavelength selecting filter such as a spectrum filter.

While the light (L$\lambda$1) having the first wavelength and the light (L$\lambda$2) having the second wavelength may each be light having a single wavelength, adoption of light having multiple wavelengths, each having a bandwidth for a wavelength, is preferred, taking into consideration ease of acquisition of the light source, such as an LED, and cost. Such light preferably has a center wavelength (wavelength with a peak intensity) of $\lambda$1 or $\lambda$2.

In the present invention, the light (L$\lambda$1) is light having a wavelength that has an absorbability with respect to a chemical component subject to concentration measurement. In contrast, the light (L$\lambda$2) is a light having a wavelength that has no or substantially no light absorbability with respect to the chemical component, or an absorbability with respect to the chemical component that is relatively lower than that of the light (L$\lambda$1).

In the present invention, a light such as the light (L$\lambda$2) is preferably adopted since measurement accuracy increases when there is no absorbability with respect to the chemical component or to the extent the absorbability differs from that of the light (L$\lambda$1).

When the concentrations of a plurality of chemical components are measured using the same object to be measured, the light (L$\lambda$1) is prepared in a quantity equivalent to the number of chemical components to be measured. That is, given N as the number of chemical components, the light (L$\lambda$1) is prepared in a quantity of n (L$\lambda$1$n$, where n is a positive integer). Among the lights (L$\lambda$1$n$: n is a positive integer), the light selected as applicable is the light having a wavelength or a wavelength range that exhibits an absorbability with respect to the one chemical component only and no or substantially no absorbability with respect to any other chemical component. As the light source of the light source portion, needless to say, a light source that emits light according to these conditions is selected and used.

The light (L$\lambda$1) and the light (L$\lambda$2) are irradiated onto the object 104 to be measured in accordance with a time-sharing method.

The light (L$\lambda$1) and the light (L$\lambda$2) are preferably irradiated onto the same optical axis or substantially the same optical axis when irradiated onto the object 104 to be measured. That is, even when a chemical component subject to concentration measurement has a spotted distribution or an uneven distribution spatially or temporally in the object 104 to be measured, when the positions in which the light (L$\lambda$1) and the light (L$\lambda$2) pass through the object 104 to be measured are the same or substantially the same, the measurement period is, at the same time, extremely short, resulting in the advantage of achieving a highly accurate measurement minimally affected by measurement errors.

An irradiated light 103 formed by the light (L$\lambda$1) or the light (L$\lambda$2) is irradiated onto the object 104 to be measured and, as a result, a transmitted light 105 exits from the exact opposite side of the object 104 to be measured.

The transmitted light 105 enters a light-receiving surface of a light-receiving sensor located in the light-receiving sensor portion 106.

The light-receiving sensor portion 106 outputs an electric signal 107 in response to the received light.

The signal 107 is either a signal 107$a$ based on the light (L$\lambda$1) or a signal 107$b$ based on the light (L$\lambda$2).

The signal 107$a$ and the signal 107$b$ are input to the differential signal forming portion 108 either sequentially based on a set time difference or simultaneously.

When input based on a set time difference, the signal input first may, depending on the case, be held for a predetermined period in a predetermined circuit inside the differential signal forming portion 108 in accordance with a timing for forming the differential signal.

A differential output signal 109 output from the differential signal forming portion 108 in accordance with the input of the signal 107 is transferred to the signal storage/processing portion 110 and stored/processed so as to output an output signal 111.

The output signal 111 is transferred to the display unit 112. The display unit 112 that received the output signal 111 displays a concentration display of the measured chemical component on a display screen of the display unit 112 as a value corresponding to the output signal 111.

The above series of processes is controlled by the control unit 113 in accordance with instructions from the operation portion 114.

The light-receiving sensor constituting the light-receiving sensor portion 106 may be a single element such as a photodiode, or a line sensor or area sensor in which a predetermined number of light-receiving pixels is one-dimensionally or two-dimensionally disposed, respectively.

When the chemical component to be measured is not uniform in the object 104 to be measured, a measurement error resulting from positional dependency may decrease the measurement accuracy, and thus adoption of a line sensor or an area sensor is preferred. In particular, adoption of an area sensor that has a light-receiving surface having a size that covers an exiting surface from which the transmitted light 105 exits, orthogonal to the optical axis of the object 104 to be measured, can significantly increase measurement accuracy, and is thus preferred.

While the light (L$\lambda$1) and the light (L$\lambda$2) have each been described using a light having a single wavelength, the wavelength is not necessarily limited thereto in the present invention, and the wavelength may have a bandwidth (wavelength range). That is, in the present invention, a luminous flux having a predetermined wavelength range may be used.

Next, an example of actual optical concentration measurement using the system 100 in FIG. 2 will be described on the basis of FIGS. 3 and 4.

FIG. 3 is a flowchart for explaining a preferred embodiment of the optical gas concentration measuring method according to the present invention.

When a button switch of the operation portion 114, or the like, for starting measurement is pressed, concentration measurement is started (step 201).

In step 202, the existence or absence of the specimen 104 serving as the object to be measured, including if the specimen 104 is appropriately placed in a predetermined position, is determined. When it is determined that the specimen 104 has been appropriately placed, the first light (L$\lambda$1) and the second light (L$\lambda$2) necessary and appropriate for measuring the concentration of a chemical component to be measured in the specimen 104 are selected in step 202.

Selection of the first light (Lλ1) and the second light (Lλ2) is made by setting the light source 101a for the first light (Lλ1) and the light source 101b for the second light (Lλ2) in predetermined positions in the optical gas concentration measuring system 100, or dispersing the light using a spectroscope.

When selection is based on the establishment of a light source, selection of the first light (Lλ1) and the second light (Lλ2) can be made in advance from an absorption spectrum of the chemical component to be measured in the specimen 104, allowing step 203 to be performed before step 201.

Next, in step 204, acquisition of an analytical curve for deriving the concentration value of the chemical component to be measured based on measurement data is started.

The analytical curve can be acquired by reading the data of an analytical curve stored in advance in a storage portion of the optical gas concentration measuring system 100, or by creating a new analytical curve as described in FIG. 5.

Once acquisition of the analytical curve is complete, measurement of the specimen 104 is started as indicated in step 206.

When measurement is started, the first light (Lλ1) and the second light (Lλ2) are irradiated onto the specimen 104 for a predetermined period by time-sharing at a predetermined interval.

The first light (Lλ1) and the second light (Lλ2) that passed through the specimen 104 are received by a light-receiving sensor set in the light-receiving sensor portion 106 (step 207).

When the light-receiving sensor receives each transmitted light of the first light (Lλ1) and the second light (Lλ2) by time-sharing, an output signal of a size corresponding to the amount of received light is output each time light is received. In accordance with this output signal, "−log (1−ΔT)" is calculated (step 208).

Next, in step 209, whether or not "−log (1−ΔT)" is in the range of the analytical curve is determined.

If "−log (1−ΔT)" is within the range of the analytical curve, the concentration of the targeted chemical component in the specimen 104 is derived on the basis of the analytical curve data (step 210).

FIG. 4 is a timing chart for explaining a signal output timing of the example in FIG. 3. That is, FIG. 4 is a timing chart showing the time responses of an output OUT1 of the first light source 101a, an output OUT2 of the second light source 101b, an output OUT3 of the light-receiving sensor, an output OUT4 of the differential signal, and a gas concentration GC.

The state of the gas concentration GC that increases in stages with time can, for example, be measured as a change in concentration of the target gas obtained by detecting an output signal (differential signal output OUT4) at timings T1 to T4 illustrated in FIG. 4 and deriving the value from the detected output signal value and the analytical curve acquired in advance.

When the output OUT1 of the first light source and the output OUT2 of the second light source are output on the same axis at mutually predetermined and repeated intervals at timings such as illustrated in FIG. 4, the gas to be measured does not exist before timing T1, and thus the output OUT3 of the light-receiving sensor is output as pulses S11, S21 having the same size.

During the period between timings T1 and T2, the period between timings T2 and T3, and the period between the timings T3 and T4, the pulses S12, S22, S13, S23, S14, S24 are output. While the sizes of the pulses S12, S13, S14 are the same as the size of the pulse S11, the sizes of the pulses S22, S23, S24 decrease in stages in accordance with the level of light absorption of the gas to be measured.

That is, because the light from the second light source is absorbed in the gas to be measured and the amount of light received by the light-receiving sensor gradually decreases in accordance with the gas concentration, the sizes of the pulses S22, S23, S24 decrease in stages in accordance with the level of concentration of the gas to be measured.

FIG. 5 explains an example of a method for acquiring an analytical curve in advance, prior to measurement of the gas concentration. FIG. 5 is a flowchart for finding the analytical curve.

To acquire the analytical curve, an analytical curve acquiring device is used.

When acquisition of the analytical curve is started (step ST1), whether or not an optical measuring cell has been prepared is determined in step ST2.

Once the optical measuring cell has been prepared, the flow proceeds to step ST3. In step ST3, whether or not a predetermined carrier gas has been introduced into the cell interior in a predetermined unit amount is determined.

When it is determined that the predetermined carrier gas has been introduced into the cell interior in a predetermined unit amount, the flow proceeds to step ST4.

This step of determining whether or not the carrier gas has been introduced may be omitted, or the step may be changed to a step for determining if the cell interior has reached a predetermined degree of vacuum. This determination of whether the cell interior has reached a predetermined degree of vacuum may be omitted as well.

In either case, the cell interior needs to be cleaned before proceeding to step ST4 in order to acquire a more accurate analytical curve.

In step ST4, a plurality of gases subject to concentration measurement is sequentially introduced into the cell, and the absorbance of the gas of each concentration is measured.

Once measurement is completed, the flow proceeds to step ST5.

In step ST5, the analytical curve is created on the bases of the absorbance measurement data.

FIG. 6 illustrates an example of an analytical curve created in this way.

FIG. 6 is a graph showing a relationship between the gas concentration GC and "−log (1−ΔT)."

Once the analytical curve is created, the flow can transition to concentration measurement of the specimen.

Next, several preferred embodiments of the optical gas concentration measuring system that embodies the gas concentration measuring method according to the present invention will be described using FIGS. 7 to 10.

FIG. 7 is an example of gas concentration measurement by transmitted light.

In a main component 500, the light source portion comprises the first light source 101a that emits the first light (Lλ1) and the second light source 101b that emits the second light (Lλ2).

The first light (Lλ1) emitted from the first light source 101a is focused on the optical axis by the light-focusing optical portion 102, passed along the optical axis as an irradiated light 103a, and irradiated onto the object 104 to be measured. The amount of the irradiated light 103a not absorbed in the object 104 to be measured exits the object 104 to be measured as a transmitted light 10a.

The transmitted light 105a enters the light-receiving surface of the light-receiving sensor portion 106. When the transmitted light 105a is received by the light-receiving sensor portion 106, the electric signal 107 photoelectrically converted in accordance with the amount of the transmitted light 105a is output from the light-receiving sensor portion 106. The signal 107 output from the light-receiving sensor portion 106 is input to the differential signal forming portion 108 configured by a differential signal forming circuit.

The second light (Lλ2) emitted from the second light source 101b is passed along the optical axis as an irradiated light 103b and irradiated onto the object 104 to be measured in the same way as the first light (Lλ1), and a transmitted light 105b exits the object 104 to be measured accordingly.

In the case of the second light (Lλ2), the light is either not absorbed in the object 104 to be measured, or absorbed with a low absorbability compared to the first light (Lλ1). Thus, the amounts of the irradiated light 103b and the transmitted light 105b are either the same or substantially the same, or the difference thereof is less than the difference between the irradiated light 103a and the transmitted light 105a.

FIG. 7 is an explanatory schematic configuration view for explaining main components of another preferred embodiment of the optical gas concentration measuring system that embodies the gas concentration measuring method of the present invention. Except for the fact that FIG. 7 is an example of measurement by reflected light while FIG. 6 is an example of measurement by transmitted light, the example in FIG. 7 is the same as that in FIG. 6, and thus a detailed description thereof will be omitted.

FIG. 8 is an explanatory schematic configuration view for explaining main components of yet another preferred embodiment of the optical gas concentration measuring system that embodies the gas concentration measuring method of the present invention.

Except for the fact that FIG. 8 is an example of measurement by reflected light while FIG. 7 is an example of measurement by transmitted light, the example in FIG. 8 is the same as that in FIG. 7, and thus a detailed description thereof will be omitted.

FIG. 9 is an explanatory schematic configuration view for explaining a main component of yet another preferred embodiment of the optical gas concentration measuring system that embodies the gas concentration measuring method of the present invention. Except for the fact that FIG. 9 is an example of measurement by diffused light while FIG. 7 is an example of measurement by transmitted light, the example in FIG. 9 is the same as that in FIG. 7, and thus a detailed description thereof will be omitted.

FIG. 10 is an explanatory schematic configuration view for explaining a main component of yet another preferred embodiment of the optical gas concentration measuring system that embodies the gas concentration measuring method of the present invention. Except for the fact that FIG. 10 adopts a branch-type optical fiber 801 for the light-focusing optical portion 102 in the example in FIG. 7, the example in FIG. 10 is the same as that in FIG. 7, and thus a detailed description thereof will be omitted.

FIG. 11 illustrates a circuit diagram for explaining a preferred example of the differential signal forming portion adopted in the present invention.

A differential signal forming portion 900 comprises a (charge) integrating amplifier 902, a sample/hold circuit 903, and a differential amplifier 904.

When the transmitted light, reflected light, or scattered light produced upon irradiation of light having a predetermined wavelength for concentration measurement onto the object 104 to be measured subject to concentration measurement, such as a fruit or a vegetable, is received by a photodiode 901 for light reception, an electric signal P1 corresponding to the amount of received light is output from the photodiode 901. The electric signal P1 is input to the integrating amplifier 902.

The integrating amplifier 902 is provided for sensitivity enhancement so as to allow measurement down to subtle changes in gas concentration of the specimen 107.

The output signal of the integrating amplifier 902 is input to the sample/hold circuit 903.

A sampled/held analog signal is input to the differential amplifier 904.

Gas Concentration Measurement Example Embodying Present Invention

Next, an example that embodies the present invention will be described using a gas concentration measurement example.

A preferred embodiment of the concentration measuring method for measuring concentration by using a plurality of lights having different wavelengths and irradiating the plurality of lights by time-sharing will now be described.

In the following, a preferred embodiment of a gas concentration measurement example that uses transmitted light for measurement will be primarily described.

Cases where reflected light or scattered light is used for measurement rather than transmitted light, needless to say, also fall into the category of the present invention, and are naturally within the technical field.

To embody the present invention as a gas concentration measuring device, the measuring device may comprise a regular light source, a photodiode of a light-receiving element, electronic circuit components, and the like that are easily acquirable, based on a premise of compatibility with the measurement target, and thus in the following descriptions matters obvious to persons skilled in the art will be omitted and main points will be simplified.

The specimen (object to be measured) is, for example, a gas that flows through a gas pipe.

The gas pipe (gas supply line) is provided with an incident surface into which light (a measured light hλ) used for measurement enters, and an exiting surface from which light, having passed through the gas pipe, exits to the outside.

The incident surface and the exiting surface are made of a material having a transmittance of "1" or substantially "1" with respect to the measured light hλ.

Regardless of whether the gas that flows through the gas pipe is a single type or a plurality of types of mixtures, the measuring device can measure the concentration of the target gas.

In the following, the case of the single type is described using trimethylgallium (TMGa), for example, as the gas serving as the specimen.

Other examples of the specimen gas type include trimethylindium (TMIn) and titanium tetrachloride (TiCl4).

In the gas concentration measurement of trimethylgallium (TMGa), an LED that emits light (Lλ1) having a center light wavelength of 500 nm is adopted as the first light source 101a, for example, and the light intensity thereof is 1.0 mW/cm$^2$/m.

An LED that emits light (Lλ2) having a center light wavelength of 230 nm is adopted as the second light source 101b, and the light intensity thereof is 1.0 mW/cm$^2$/nm.

In the present invention, the light (Lλ1) 103a emitted from the first light source 101a and the light (Lλ2) 103b emitted from the second light source 101b are transmitted through the specimen 104 at separate times (by time-sharing), and enter the light-receiving sensor of the light-receiving sensor portion 106. As the light-receiving sensor, a photodiode (S1336-18BQ) manufactured by Hamamatsu Photonics K.K, for example, may be used. The received light sensitivity of the light-receiving sensor in this case is 0.26 A/W at a light wavelength of 500 nm, and 0.13 A/W at a light wavelength of 230 nm.

The output signal 107 of the light-receiving sensor portion 106 is input to the differential signal forming circuit 108, and the output signal 109 is output from the differential signal forming circuit 108 accordingly.

A light source that emits light having an absorbance that changes depending on the concentration of the gas of the specimen 104, and a light source that emits light having an absorbance that does not or substantially does not change depending on the concentration of the gas of the specimen 104 are adopted as the first light source 101a and the second light source 101b, respectively.

While the above gas concentration measurement example has been described using the configuration in FIG. 7 that measures transmitted light, naturally the measurement can be applied to the configuration in FIG. 8 that uses a reflected light and to the configuration in FIG. 9 that uses a scattered light without having to particularly re-describe the details.

Further, while an optical path of the first light source 101a and an optical path of the second light source 101b differ in the object 104 to be measured if the light-focusing optical portion 102 does not exist in the configuration illustrated in FIG. 7, preferably the first light source 101a and the second light source 101b are arranged as close to each other as possible so as to bring the optical paths as close to the same optical path as possible.

Or, the optical paths can be made substantially identical when the branch-type optical fiber 801 is adopted as illustrated in FIG. 10 in place of the light-focusing optical portion 102, and thus adoption of the branch-type optical fiber 801 is preferred.

FIG. 11 is a configuration diagram for explaining a configuration of a preferred example of the differential signal forming circuit.

The differential signal forming circuit 900 illustrated in FIG. 11 is provided with the (charge) integrating amplifier 902 to increase sensitivity so that subtle changes in the gas concentration of the specimen 107 can be measured.

The output signal of the (charge) integrating amplifier 902 is input to the sample/hold circuit 903.

A sampled/held analog signal is input to an analog-digital converter (ADC) 1301. An optical signal based on the first light source, an optical signal based on the second light source, and a differential signal between these two signals are output from the ADC 1301.

FIG. 4 is a timing chart showing the time responses of an output OUT1 of the first light source 101a, an output OUT2 of the second light source 101b, an output OUT3 of the light-receiving sensor, an output OUT4 of the differential signal, and a gas concentration GC.

Here, "output of the light source" is the amount of light emitted during the ON period and, when the light has high directivity, is substantially equivalent to the amount of light received by the light-receiving sensor.

In the present invention, each light from the light sources 101a, 101b can be focused by the light-focusing optical portion 102 as illustrated in FIGS. 7 to 9, or a branch-type optical fiber 801 can be adopted as illustrated in FIG. 10, and thus as long as the light sources 101a, 101b are arranged by bringing an emitting surface of the light sources 101a, 101b near or in contact with an incident surface of the light-focusing optical portion 102 or an incident surface of the branch-type optical fiber 801, it is possible to make the amount of light emitted during the ON period of each of the light sources 101a, 101b close to or substantially equivalent to the amount of light received by the light-receiving sensor.

In general, absorbance is given based on the following formula:

[Formula 1]

$$-\log\left(\frac{I}{I_{\Box 0}}\right) = -\log(1 - \Delta T) = \alpha K \quad (1)$$

Here, "$I_0$" indicates the intensity of the incident light, "I" indicates the intensity of the transmitted light, and "K" indicates the gas concentration. $\alpha$ is a coefficient and is determined by an optical path length in the specimen 104, a light absorption coefficient of the gas subject to concentration measurement in the specimen 104, and the like.

Further, "$\Delta T$" indicates the absorbance difference. In this embodiment, the optical path lengths are set so that $\alpha$ is substantially "0" for the first light source 101a, and 2.18× 10-4/ppm for the second light source 101b. Given "$I_1$" as the intensity of the transmitted light of the light (L$\lambda$1) emitted from the first light source 101a and "$I_2$" as the intensity of the transmitted light of the light (L$\lambda$2) emitted from the second light source 101b, formula (1) can be modified to formula (2) when "$I_1$" uses the fact that the transmittance difference with respect to the light wavelength of the first light source, regardless of gas concentration, is substantially "0".

[Formula 2]

$$-\log(1 - \Delta T) = -\log\left(1 - \frac{X}{I_1}\right) = \alpha K \quad (2)$$

Here, "X" is the output value of the differential signal, and is equivalent to "$I_2 - I_1$."

According to this formula, the absorbance of the specimen 104 can be measured with high accuracy using the output OUT1 of the first light source 101a having an absorptivity that changes in accordance with the gas concentration, and the output OUT2 of the second light source 101b having an absorptivity that does not change in accordance with the gas concentration.

Thus, there is no need to measure gas concentrations to create an analytical curve for each measurement using known reference samples.

A gas densitometer can measure changes in absorptivity in a stable manner, even if there are changes in the measurement system, gas temperature, or the like.

Setup is performed so that an integrated charge (1) of the integrating amplifier 902 based on the first light source 101a and the integrating charge (2) of the integrating amplifier 902 based on the second light source 101b when the gas concentration is "0" are equal or substantially equal.

Here, in this embodiment, an integration period (1) during output of the first light source 101a and an integration period (2) during output of the second light source 101b were adjusted so that the charges were 6.1×10−9 C.

The integration period (1) and the integration period (2) of this embodiment were set to 4.0 msec and 2.0 msec, respectively.

FIG. 15 shows a relationship between an absorbance value measured with respect to a gas concentration and a value equivalent to three times a standard deviation of a noise superimposed on the measured signal at this time.

Further, when measurement was made using this charge, the main noise component was confirmed as photon shot noise.

Based on the results, when the charge value is $6.1 \times 10^{-9}$ C, the effect of the photon shot noise proportional to the square root of the signal charge became relatively small, making it possible to measure an absorbance difference $\Delta T$ up to $5 \times 10^{-5}$ with 99% reliability. That is, the gas concentration could be measured to an accuracy of 0.1 ppm.

Further, according to the embodiment of the present invention, output is obtained from a difference between signals based on two lights having different wavelengths, even if the temperature changes, making it possible to cancel an amount of fluctuation in a transmittance that changes according to temperature. Thus, even if there is temperature fluctuation during measurement, stable sensitivity can be achieved with high accuracy.

In the present invention, a communication module for short-range communication, such as WiFi, Bluetooth (registered trademark), or Near Field Communications (NFC), or a communication module for satellite communication is incorporated in the gas concentration measuring device that embodies the present invention, making it possible to make the gas concentration measuring device function as an information terminal device on a network.

For example, a non-destructive, small-sized gas concentration measuring device according to the present invention featuring a small size, light weight, and ease of use is set in a gas supply line on a semiconductor manufacturing line, making it possible to monitor the gas flow during semiconductor manufacture and if a predetermined gas is supplied at the prescribed unit flow rate (flow rate per unit time) and flow rate ratio.

With a communication module capable of wireless or wired communication assembled in the small-sized gas concentration measuring device, concentration changes in the predetermined gas can be transmitted hourly to a central control system of the manufacturing line, and the gas concentration can be appropriately controlled and adjusted from a central control system on the basis of transmitted data.

In this system, when a large number of small-sized gas concentration measuring devices are set on the manufacturing line and a semiconductor is manufactured, network management can be easily achieved, making it possible to exhibit performance more effectively.

While FIG. 11 illustrates a preferred example of the differential signal forming portion (circuit configuration) in the realization of the present invention, the present invention is not limited thereto, allowing adoption of the differential signal forming portions (circuit configurations) illustrated in FIGS. 12 to 14 as preferred examples as well.

In FIGS. 12 to 14, components that fulfill the same functions as those denoted with the reference numerals in FIG. 11 are denoted using the same reference numerals as FIG. 11.

The configuration illustrated in FIG. 12 is the same as that in FIG. 11 except that, in addition to a circuit for a differential signal output 905, a circuit for a pre-differential signal output 906 has been added.

With the addition of the circuit for the pre-differential signal output 906, there is the advantage that, compared to the configuration illustrated in FIG. 11, even if fluctuation occurs in the absolute value of absorbance due to temperature change or the like, or temporal fluctuation occurs in the light output of the light source, the amount of these fluctuations can be measured and calibrated.

In FIG. 13, compared to FIG. 12, there are two systems in which a signal is transmitted from a sample/hold circuit (903a, 903b) to a differential amplifier (904a, 904b), and an ADC 1301 is further provided. A signal output 1302 A/D converted by the ADC 1301 is output.

This configuration results in the advantage of being able to eliminate the offset of the integrating amplifier compared to that in FIG. 12.

FIG. 14 is an example of a circuit designed in more detail than the example in FIG. 13.

In this example, an integrating (accumulation) amplifier portion 1401, which is similar to the integrating amplifier 902, and a 1/10× amplifier portion 1402 are provided. In addition, the differential amplifier portions 904a, 904b are each provided with two instrumentation amplifiers for differential output.

Such a configuration results in the advantage of being able to eliminate the offset of the differential amplifiers.

That is, given the differential signal indicated in formula (2) described above as:

$$G \times (\Delta 6 - \Delta 4) - G \times (\Delta 5 - \Delta 3) \tag{3}$$

G: Amplification factor of differential amplifier using an instrumentation amplifier (AD8222)

The difference between the signals of the combinations ($\Delta 6$ and $\Delta 4$) and ($\Delta 5$ and $\Delta 3$) having a small signal level difference is amplified. Subsequently, the difference is further obtained, making it possible to obtain a minute difference in a large signal range with high accuracy.

Next, an example of a preferred embodiment of gas flow path device for gas concentration measurement according to the present invention will be described.

FIG. 16 schematically shows an outline of a gas flow path device 1600 for gas concentration measurement.

The gas flow path device 1600 comprises a gas concentration measuring cell 1601. The gas concentration measuring cell 1601 is provided with a gas flow path 1602. A gas introduction path 1603 for introducing the gas to the gas flow path 1602 is provided on a gas flow path upstream side, and a gas leading path 1604 for leading the gas inside the gas flow path 1602 is provided on a gas flow path downstream side.

A light introduction window 1607 is provided on the upstream side of the gas flow path 1602 to irradiate the light for gas concentration measurement emitted from a light source 1605 onto the gas inside the gas flow path 1602. A light-receiving window 1608 is provided on the downstream side of the gas flow path so that the light for gas concentration detection is irradiated onto a light-receiving element 1606 for detection.

The gas introduced from the gas introduction path 1603 flows (illustrated by the arrow B) in the gas flow path 1602 in the irradiation direction (illustrated by the arrow A) of the light emitted from the light source 1605.

In the present invention, the gas flow path 1602 is preferably a structure that advances linearly, such as a circular or rectangular cylinder having a straight shape.

Preferably, the material constituting the light introduction window 1607 and the light-receiving window 1608 is a material that effectively transmits the measured light. Such a material does not require exposure compensation due to absorption by the light introduction window 1607 and the light-receiving window 1608.

When light having a short wavelength, such as UV light, is used as the measured light, a material that transmits UV light such as sapphire is used.

The wavelength of the light emitted from the light source 1605 is selected as desired from a wavelength range that does not cause decomposition, polymerization, the breaking of interatomic bonds, or the like upon absorption of the gas subject to concentration measurement.

Preferably, a light having a wavelength range that absorbs the gas subject to concentration measurement but does not produce a chemical reaction, such as decomposition, is used.

The gas concentration measuring cell 1601 allows measurement of the concentration of a preferred gas using the optical gas concentration measuring system 100 as long as the gas concentration measuring cell 1601 is set in the position of the specimen 104 of the optical gas concentration measuring system 100 illustrated in FIG. 2, for example.

Or, with the light source 1605 and the photodetector 1606 set in predetermined positions (the gas concentration measuring device 1600), the gas concentration measuring cell 1601 may be set and used in the position of the gas concentration measuring device illustrated in FIG. 17.

In the present invention, signals (the electric signals 107, 107a, 107b, for example) formed on the basis of the output signal from a light-receiving element, such as a photodiode or a phototransistor, serving as a component of the light-receiving sensor portion 106 and the photodetector 1606 are preferably established as voltage signals for alleviating electrical noises that can occur in an electric circuit, to the extent possible.

The signals inside the differential signal forming portion (900, 1000, 1300, 1400) are also preferably formed or processed as voltage signals, to the extent possible.

FIG. 17 illustrates an example of a gas supply device that is provided with the gas concentration measuring device of the present invention, and supplies gas while monitoring the gas concentration.

A gas supply device 1700 is a gas supply system comprising a bubbling function having the function of measuring the concentration of a gas of a sublimable chemical substance.

In FIG. 17, the gas supply device 1700 comprises a bubbling device 1700-1 and a gas supply portion 1700-2.

In the bubbling device 1700-1, a source tank 1704 into which the raw material of the concentration measurement gas is delivered is included in a constant-temperature water tank 1703.

The gas supply portion 1700-2 comprises a supply line of an inert gas for the concentration measurement gas, such as N2, and a supply line for a concentration measurement gas supplied from the bubbling device 1700-1.

The inert gas introduced from a gas introduction pipe 1711 can be supplied upon division into three supply lines.

A first supply line 1707 is a purge line, and is a gas supply line used when purging the gas flow path inside gas concentration measurement means 1710.

In the first supply line 1707, a mass flow controller 1701-1, a valve 1702-1, and a valve 1702-4 are arranged sequentially in predetermined positions from the upstream side of the gas flow.

A second supply line 1708 is a gas supply line for appropriately diluting the concentration measurement gas. In the second supply line 1708, a mass flow controller 1701-2, a valve 1702-2, a pressure gauge 1706, a mass flow controller 1701-4, and a valve 1702-5 are arranged sequentially in predetermined positions from the upstream side.

The first supply line 1707 and the second supply line 1708 are merged downstream of the valve 1702-4 and the valve 1702-5, and connected with the gas concentration measurement means 1710.

The second supply line 1708 is provided with an exhaust line 1713-1 for gas exhaust between the mass flow controller 1701-4 and the valve 1702-5.

The gas is exhausted by the opening and closing of a valve 1702-6.

Further, the mass flow controller 1701-4 is also provided with a gas exhaust line 1713-2, and the gas is exhausted in accordance with the degree to which a valve 1702-7 is opened or closed.

A third supply line 1709 is a gas supply line for supplying the bubbled and supplied gas subject to concentration measurement.

The third supply line 1709 is connected to the second supply line 1708 between the pressure gauge 1706 and the mass flow controller 1701-4.

In the third supply line 1709, a valve 1702-3 and a pressure controller 1705 are arranged in predetermined positions from the upstream side.

During bubbling, the inert gas supplied from a mass flow controller 1701-3 is passed through a bubbling gas introduction line 1714-1 connected midway on the third supply line 1709, and introduced into a raw material liquid 1715 inside the source tank 1704.

The raw material liquid 1715 is a raw material of the gas to be measured, and may be liquefied gas components or a solution obtained by dissolving gas components into a solvent.

Valves 1702-8, 1702-9 are arranged in the bubbling gas introduction line 1714-1.

The bubbling gas produced inside the source tank 1704 by bubbling is passed through a bubbling gas leading line 1714-2 and supplied to the third supply line 1709.

A downstream end of the bubbling gas leading line 1714-2 is connected to the third supply line 1709 between the valve 1702-3 and the pressure controller 1705.

In the bubbling gas leading line 1714-2, valves 1702-10, 1702-11 are arranged sequentially from the upstream side.

The gas concentration measurement means 1710, for example, uses the gas concentration measuring device 1600 as described above.

A Fourier transform infrared spectrophotometer (FT-IR) 1712 is provided downstream of the gas concentration measurement means 1710.

The gas that passed through the FT-IR 1712 is to be introduced into a reaction chamber for film formation or the like, for example, and is thus further supplied to the downstream side (arrow 1700A).

The FT-IR 1712 is provided as necessary, and is thus not required in the present invention.

The FT-IR 1712 is provided when comparison with a measured value of the gas concentration measurement means 1710 is required.

In the present invention, when the concentration of a gas of a chemical material having a relatively high gasification temperature, such as a material having a high boiling point or sublimability, is to be measured, preferably at least the gas concentration measuring device 1600 and the gas concentration measuring cell 1601 are kept at a temperature that allows the measured gas to maintain a gas state.

For example, preferably the gas concentration measuring device 1600 and the gas concentration measuring cell 1601 are arranged in an atmosphere having an environment temperature that allows the measured gas to maintain a gas state, or heating means, such as a heater, is provided in a location appropriate to the gas concentration measuring device 1600 and the gas concentration measuring cell 1601 so that at least the ambient temperature in the gas flow path 1602 inside the gas concentration measuring cell 1601 is kept at a temperature that allows the measured gas to maintain a gas state.

Next, an example of actual measurement using the device illustrated in FIG. 17 will be described.

First, as measurement preparation, the gas distribution line is purged using nitrogen (N2) gas having no absorption in UV light (the measurement light to be used) before an MO material such as trimethylgallium (TMGa) is supplied in a gas state via the mass flow controller (MFC1) 1701-1 into the gas distribution line.

At this time, the valve 1702-7 is open, the valve 1702-6 is open, the valve 1702-5 is closed, and the valve 1702-4 is open.

During this period, N2 gas is supplied into the source tank by the mass flow controller (MFC3) 1701-3, and caused to bubble.

The flow rate ratio of the mass flow controllers (MFC2) 1701-2, 1701-3 is controlled, changing the gas concentration of the MO material (during analytical curve creation).

As a result, the flow rate of the gas supplied to the measuring cell provided in the gas concentration measurement means 1710 changes, and thus the remaining gas is discharged outside via the valve 1702-7 at a constant flow rate by the mass flow controller (MFC4) 1701-4.

To ensure that the gas concentration of the MO material is constant, the nitrogen purge is required even when the gas of the MO material is not supplied to the measuring cell.

During measurement, the valve 1702-6 is closed, the valve 1702-5 is opened, and the valve 1702-4 is closed simultaneously, and the gas of the MO material is supplied into the measuring cell.

After measurement, the valve 1702-4 is opened, the valve 1702-5 is closed, and the valve 1702-6 is opened simultaneously, replacing the gas in the gas distribution line with nitrogen gas.

Next, an example in which the actual measured value is fed back to control the flow rate ratio and the like will be described.

In FIG. 17, the flow rate of the mass flow controller (MFC2) 1701-2 is changed when the monitor concentration deviates from the target concentration, controlling the flow rate so as to decrease the deviation. That is, the flow rate of the mass flow controller (MFC2) 1701-2 is increased when the target concentration is high, and decreased when then the target concentration is low (case A).

Or, the internal pressure of the tank 1704 is changed. That is, a control pressure of a pressure controller (UPCUS) 1705 is increased to increase the internal pressure of the tank 1704 when the target concentration is high, and decreased to decrease the internal pressure of the tank 1704 when the target concentration is low (case B).

When the capacity of the tank 1704 is large, preferably case A, which can address the issue in a short period of time, is selected to perform control.

FIG. 15 illustrates the relationship between the value of the absorbance measured for the concentration of the gas (TMGa), and the value equivalent to three times the standard deviation of the noise superimposed on the measured signal.

FIG. 18 is a schematic configuration view for explaining a preferred example of the production line of an electronic device to which the gas concentration measuring method of the present invention is applied. In FIG. 18, components that are same as those in FIG. 17 are denoted using the reference numerals of FIG. 17.

FIG. 18 differs from FIG. 17 in that the monitoring and control of the gas flow rate of a production line 1800 are performed on the basis of instructions from a central monitoring and control system 1803 located in a central control room 1802.

Communication between the production line 1800 and the central monitoring and control system 1803 located in the central control room 1802 is performed wirelessly. Naturally, use of wired communication means is also acceptable.

Mass flow controllers (1801-1 to 1801-3), a pressure controller 1805, and the gas concentration measurement means 1710 of the production line 1800 are each provided with communication means (1806-1 to 1806-6) having the function of communicating with communication means 1804, comprising a wireless antenna, and controlling the device.

Each valve illustrated in FIG. 18, although not shown, is provided with the same communication means as the communication means (1806-1 to 1806-6), and valve opening/closing control is performed on the basis of instructions from the central monitoring and control system 1803.

DESCRIPTIONS OF REFERENCE NUMERALS

100 Optical gas concentration measuring system
100-1 Optical gas concentration measuring sub-system
100-2 Control/Operation sub-system
100-3 Optical gas concentration measuring device
101 Light source portion
101a, 101b Light source
102 Light-focusing optical portion
103, 103a, 103b Irradiated light
104 Object to be measured
105, 105a, 105b Transmitted light
106 Light-receiving sensor portion
107, 107a, 107b Electric signal
108 Differential signal forming portion
109 Differential output signal
110 Signal storage/processing portion
111 Output signal
112 Display unit
113 Control unit
114 Operation portion
201 to 211 Step
500, 600, 700, 800 Optical gas concentration measuring system
801 Branch-type optical fiber
801a, 801b Branch optical path
802a, 802b Irradiated light
900, 1000, 1300, 1400 Differential signal forming portion (circuit configuration)
901 Photodiode
902 Integrating amplifier
903, 903a, 903b Sample/Hold circuit
904, 904a, 904b Differential amplifier
905 Differential signal output
906 Pre-differential signal output
1301 ADC
1302 Signal output
1401 Integrating amplifier portion
1402 1/10× integrating amplifier portion
1600 Gas flow path device
1601 Gas concentration measuring cell
1602 Gas flow path 1603 Introduction path
1604 Leading path
1605 Light source
1606 Photodetector
1607 Light introduction window
1608 Light-receiving window
1700 Gas supply device
1700A, 1700B, 1700C Gas flow direction
1700-1 Bubbling device
1700-2 Gas supply portion
1701-1 to 1701-4, 1801-1 to 1801-4 Mass flow controller
1702-1 to 1702-11 Valve
1703 Constant-temperature water tank
1704 Source tank
1705 Pressure controller
1706 Pressure gauge
1707 First supply line
1708 Second supply line
1709 Third supply line
1710 Gas concentration measurement means
1711 Gas introduction pipe
1712 FT-IR
1713-1, 1713-2 Exhaust line
1714-1 Bubbling gas introduction line
1714-2 Bubbling gas leading line
1715 Raw material liquid
1800 Production line
1802 Central control room
1803 Central monitoring and control system
1804, 1806-1 to 1806-6 Communication means
Lλ1 Light having a first wavelength
Lλ2 Light having a second wavelength

What is claimed is:

1. An optical gas concentration measuring method when a chemical or physical process is to be implemented upon introduction of a raw material gas into a processing chamber from a gas supply line in which optical gas concentration measurement apparatus comprising a gas flow path is arranged in a predetermined position, the method comprising the steps of:
    irradiating light having a first wavelength that has an absorbability with respect to the raw material gas, and light having a second wavelength that has no or substantially no absorbability with respect to the raw material gas, or an absorbability that is relatively lower than that of the light having the first wavelength, along the same or substantially the same optical path and onto the raw material gas in the gas flow path using a time-sharing method;
    receiving in a photodetector a first exiting light on the basis of the light having the first wavelength and a second exiting light on the basis of the light having the second wavelength, the first exiting light and the second exiting light exiting from the optical path, in a photodetector disposed on an end edge of the optical path;
    inputting a first differential circuit input signal in accordance with a first signal based on the first exiting light, and a second differential circuit input signal in accordance with a second signal based on the second exiting light, the first signal and the second signal being output by the photodetector according to the received light, into a differential circuit; and
    comparing a measured value that is based on an output signal output from the differential circuit in accordance with the input, with data stored in advance in storage means to derive a concentration of the raw material gas, wherein
    the first signal and the second signal are formed by the photodetector in a first period (T13) that is arranged to be within a second period (T12),
    the photodetector is in an ON-state within second period (T12),
    the second period (T12) is arranged to be the same as or within a third period (T11),
    the light is irradiated onto the raw material gas within third period (T11), and
    said first, second and third periods satisfy the relationship T13<T12<T11.

2. The optical gas concentration measuring method according to claim 1, wherein the first signal and the second signal are voltage signals.

3. The optical gas concentration measuring method according to claim 1, wherein the first differential circuit input signal and the second differential circuit input signal are voltage signals.

4. An optical gas concentration measuring method when a chemical or physical process is to be implemented upon introduction of a raw material gas into a processing chamber from a gas supply line in which optical gas concentration measurement apparatus comprising a gas flow path is arranged in a predetermined position, the method comprising the steps of:
    irradiating light having the first wavelength and light having the second wavelength, each having a different light absorptivity with respect to the raw material gas, onto the raw material gas in the gas flow path using a time-sharing method;
    receiving the light of each wavelength that optically passes through the raw material gas according to the irradiation of the light of each wavelength, using a common light-receiving sensor;
    forming a differential signal between a first signal related to the light having the first wavelength and a second signal related to the light having the second wavelength output from the light-receiving sensor in accordance with the received light; and
    deriving a concentration of a chemical component of the object to be measured on the basis of the differential signal, wherein
    the first signal and the second signal are formed by the light-receiving sensor in a first period (T13) that is arranged to be within a second period (T12),
    the light-receiving sensor is in an ON-state within second period (T12),
    the second period (T12) is arranged to be the same as or within a third period (T11),
    the light is irradiated onto the raw material gas within third period (T11), and
    said first, second and third periods satisfy the relationship T13<T12<T11.

5. The optical gas concentration measuring method according to claim 4, wherein the first signal and the second signal are voltage signals.

6. The optical gas concentration measuring method according to claim 5, wherein the differential signal is a voltage signal.

* * * * *